(12) United States Patent
Naidu et al.

(10) Patent No.: US 8,383,639 B2
(45) Date of Patent: Feb. 26, 2013

(54) HIV INTEGRASE INHIBITORS

(75) Inventors: B. Narasimhulu Naidu, Durham, CT (US); Kevin Peese, Haddam, CT (US); Ira B. Dicker, Wallingford, CT (US); Chen Li, South Glastonbury, CT (US); Manoj Patel, Berlin, CT (US); Nicholas A. Meanwell, East Hampton, CT (US); Michael A. Walker, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 57 days.

(21) Appl. No.: 12/901,147

(22) Filed: Oct. 8, 2010

(65) Prior Publication Data
US 2011/0245241 A1 Oct. 6, 2011

Related U.S. Application Data

(60) Provisional application No. 61/252,047, filed on Oct. 15, 2009.

(51) Int. Cl.
*A01N 43/54* (2006.01)
*A61K 31/505* (2006.01)

(52) U.S. Cl. ........................................ 514/269; 544/319
(58) Field of Classification Search .................. 544/319
See application file for complete search history.

(56) References Cited

U.S. PATENT DOCUMENTS

| | | | |
|---|---|---|---|
| 7,037,908 B2 | 5/2006 | Naidu et al. | |
| 7,115,601 B2 | 10/2006 | Naidu et al. | |
| 7,135,467 B2 | 11/2006 | Walker et al. | |
| 7,169,780 B2 | 1/2007 | Crescenzi et al. | |
| 7,173,022 B2 | 2/2007 | Naidu et al. | |
| 7,176,196 B2 | 2/2007 | Naidu et al. | |
| 7,192,948 B2 | 3/2007 | Banville et al. | |
| 7,232,819 B2 | 6/2007 | Di Francesco et al. | |
| 7,273,859 B2 | 9/2007 | Naidu | |
| 7,414,045 B2 | 8/2008 | Crescenzi et al. | |
| 7,494,984 B2 | 2/2009 | Banville et al. | |
| 7,763,630 B2 * | 7/2010 | Naidu et al. | 514/269 |
| 7,893,055 B2 * | 2/2011 | Walker et al. | 514/230.5 |
| 7,897,592 B2 * | 3/2011 | Naidu | 514/210.02 |
| 7,897,593 B2 * | 3/2011 | Naidu et al. | 514/210.02 |
| 7,902,182 B2 * | 3/2011 | Naidu et al. | 514/210.21 |
| 8,039,458 B2 * | 10/2011 | Naidu et al. | 514/210.02 |
| 8,129,398 B2 * | 3/2012 | Beaulieu et al. | 514/267 |
| 2005/0267105 A1 * | 12/2005 | Naidu et al. | 514/230.5 |
| 2007/0129379 A1 | 6/2007 | Naidu et al. | |
| 2007/0149556 A1 * | 6/2007 | Mikamiyama et al. | 514/269 |
| 2009/0253677 A1 | 10/2009 | Beaulieu et al. | |

FOREIGN PATENT DOCUMENTS

| | | |
|---|---|---|
| EP | 1 698 628 | 9/2006 |
| JP | 2004-244320 | 9/2004 |
| WO | WO 03/062211 | 7/2003 |
| WO | WO 2005/061490 | 7/2005 |
| WO | WO 2005/061501 | 7/2005 |
| WO | WO 2005/070901 | 8/2005 |
| WO | WO 2006/103399 | 10/2006 |
| WO | WO 2006/121831 | 11/2006 |
| WO | WO 2007/014352 | 2/2007 |
| WO | WO 2007/064619 | 6/2007 |

OTHER PUBLICATIONS

U.S. Appl. No. 61/421,843, filed Dec. 10, 2010, Ueda et al.
U.S. Appl. No. 61/429,919, filed Dec. 10, 2010, Peese et al.
Colarusso, S. et al., "Suzuki Coupling at the 2-Position of Densely Functionalized Pyrimidones", Synthesis, No. 8, pp. 1343-1350 (2006).
Marcus, U. et al., "HIV: epidemiology and strategies for therapy and vaccination", Intervirology, vol. 45, Nos. 4-6, pp. 260-266 (2002) (PubMed Abstract).
Miles, K., "The growing HIV pandemic", Community Pract., vol. 78, No. 8, pp. 292-294 (2005) (PubMed Abstract).
Pace, P. et al., "Dihydroxypyrimidine-4-carboxamides as Novel Potent and Selective HIV Integrase Inhibitors", J. Med. Chem., vol. 50, No. 9, pp. 2225-2239 (2007).
Petrocchi, A. et al., "From dihydroxypyrimidine carboxylic acids to carboxamide HIV-1 integrase inhibitors: SAR around the amide moiety", Bioorganic & Medicinal Chemistry Letters, vol. 17, pp. 350-353 (2007).
Summa, V. et al., "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species", J. Med. Chem., vol. 49, No. 23, pp. 6646-6649 (2006).
van Heeswijk, R.P. et al., "Combination of protease inhibitors for the treatment of HIV-1-infected patients: a review of pharmacokinetics and clinical experience", Antivir. Ther., vol. 6, No. 4, pp. 201-229 (2001) (PubMed Abstract).

* cited by examiner

*Primary Examiner* — James O Wilson
*Assistant Examiner* — Alexander R Pagano
(74) *Attorney, Agent, or Firm* — James Epperson

(57) ABSTRACT

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

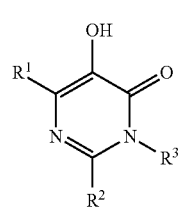

13 Claims, No Drawings

HIV INTEGRASE INHIBITORS

CROSS-REFERENCE TO RELATED APPLICATIONS

This application claims the benefit of U.S. provisional application Ser. No. 61/252,047 filed Oct. 15, 2009.

BACKGROUND OF THE INVENTION

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into four classes based on the viral protein they target and their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleoside reverse transcriptase inhibitors that behave as substrate mimics to halt viral cDNA synthesis. The non-nucleoside reverse transcriptase inhibitors, nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase is a component of the pre-integration complex of the virus that is assembled in the cell shortly after infection (Chiu, T. K.; Davies, D. R. *Curr. Top. Med. Chem.* 2004, 4, 965-977). This enzyme catalyzes the integration of proviral DNA into the host genome and is absolutely required for viral infectivity. Early experiments showed that mutating the active site of integrase within a proviral clone produces virus unable to replicate due to its inability to insert into the host chromosome (Englund, G.; Theodore, T. S.; Freed, E. O.; Engleman, A.; Martin, M. A. *J. Virol.* 1995, 69, 3216-3219). Selective HIV integrase inhibitors have been shown to possess effective anti-HIV activity in cell culture (Hazuda, D. J.; Felock, P.; Witmer, M.; Wolfe, A; Stillmock, K.; Grobler, J. A.; Espeseth, A.; Gabryelski, L.; Schleif, W.; Blau, C.; Miller, M. D. *Science*, 2000, 287, 646-650), and it is clear that this class of inhibitors is very effective as part of a combination regimen containing HIV inhibitors of different classes. An HIV integrase inhibitor, raltegravir (Isentress®), has been approved for use in treatment experienced patients based upon 48 week trial results (Cooper, D. A.; Gatell, J.; Rockstroh, J.; Katlama, C.; Yeni, P.; Lazzarin, A.; Xu, X.; Isaacs, R.; Teppler, H.; Nguyen, B. Y. *15th Conference on Retroviruses and Opportunistic Infections*, Boston, Mass., Feb. 3-6, 2008 Abst. 105LB: Evering, T. H.; Markowitz, M. *Drugs Today*, 2007, 43, 865-877). In addition, a second integrase inhibitor, elvitegravir (GS-9137), completed a successful Phase II trial in combination with ritonavir boosting in naive and treatment experienced patients (Zolopa, A. *14th Conference on Retroviruses and Opportunistic Infections*, Los Angeles, Calif. Feb. 25-28, 2007 Abst. 143LB). Thus, HIV-1 integrase is a promising target for novel anti-HIV-1 therapeutics.

The invention provides technical advantages, for example, the compounds are novel and inhibit HIV integrase. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention are compounds of Formula I

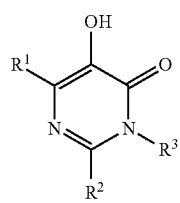

I wherein:
$R^1$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl; $R^1$ is substituted with 1 benzyl moiety which is substituted with 0-3 substituents selected from halo and alkyl; and $R^1$ is substituted with 0-2 alkyl substituents;
$R^2$ is alkoxy, alkyl, cycloalkyl, azetidinyl, pyrrolidinyl, piperidinyl, piperazinyl, N-alkylpiperazinyl, morpholinyl, or dioxothiazinyl;
$R^3$ is alkyl;
or $R^2$ and $R^3$ taken together is

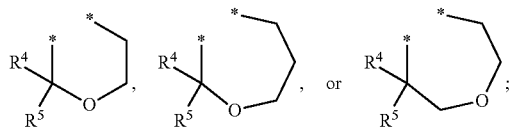

$R^4$ is hydrogen or alkyl;
$R^5$ is hydrogen or alkyl;
or $R^4$ and $R^5$ taken together is $C_{3-6}$alkylene or $CH_2CH_2OCH_2CH_2$;
or a pharmaceutically acceptable salt thereof.
Another aspect of the invention is a compound of formula I wherein:
$R^1$ is triazolyl, oxadiazolyl, imidazolyl, oxazolyl, or thiazolyl; $R^1$ is substituted with 1 benzyl moiety which is substituted with 1 halo substituent; and $R^1$ is substituted with 0-1 alkyl substituents;
$R^2$ is alkoxy, cycloalkyl, or morpholinyl;
$R^3$ is alkyl;
or $R^2$ and $R^3$ taken together is

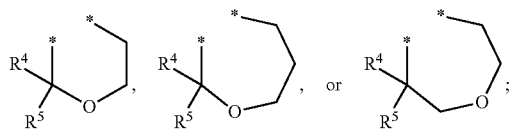

$R^4$ is alkyl; and
$R^5$ is alkyl;
or a pharmaceutically acceptable salt thereof.
Another aspect of the invention is a compound of formula I where
$R^1$ is triazolyl, N-methyltrizolyl, oxadiazolyl, imidazolyl, N-methylimidazolyl, oxazolyl, or thiazolyl, and is substituted with 1 p-fluorobenzyl moiety;
$R^2$ is ethoxy, cyclopentyl, or morpholinyl;
$R^3$ is methyl;
or $R^2$ and $R^3$ taken together is

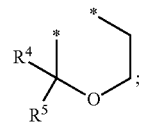

$R^4$ is methyl; and
$R^5$ is methyl;
or a pharmaceutically acceptable salt thereof.
Another aspect of the invention is a compound of Formula I where $R^1$ is triazolyl, oxadiazolyl, imidazolyl, oxazolyl, or thiazolyl; $R^1$ is substituted with 1 benzyl moiety which is substituted with 0-3 substituents selected from halo and alkyl; and $R^1$ is substituted with 0-2 alkyl substituents.
Another aspect of the invention is a compound of Formula I where $R^2$ and $R^3$ taken together is

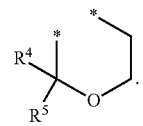

Another aspect of the invention is a compound of Formula I where $R^4$ and $R^5$ are methyl.
Another aspect of the invention is a compound of Formula I where $R^4$ and $R^5$ taken together is propylene, butylene, or $CH_2CH_2OCH_2CH_2$.
For a compound of Formula I, the scope of any instance of a variable substituent, including $R^1$, $R^2$, $R^3$, $R^4$, and $R^5$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

"Dioxothiazinyl" means

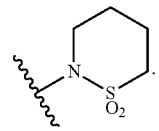

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. An example of a tautomeric pair is shown below.

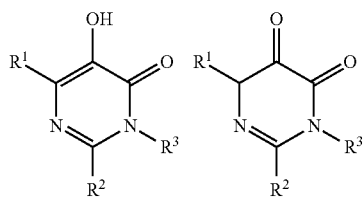

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Scheme 1

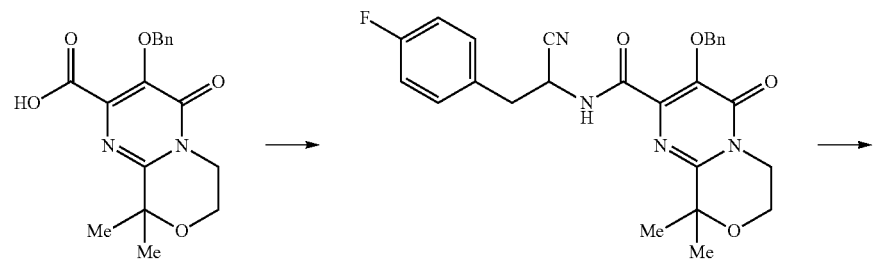

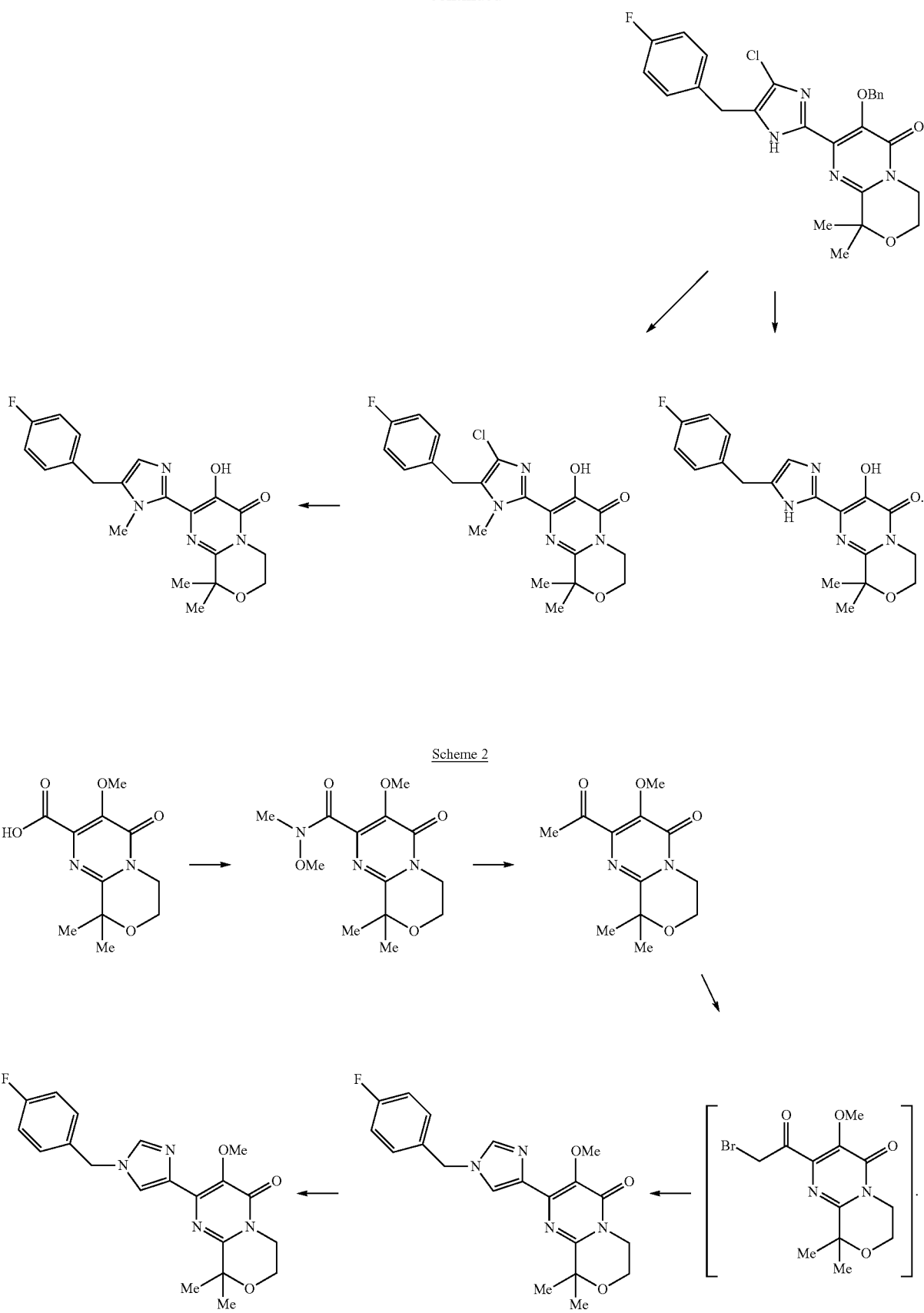

Scheme 3
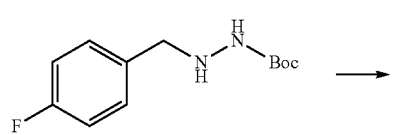
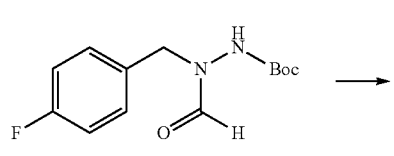
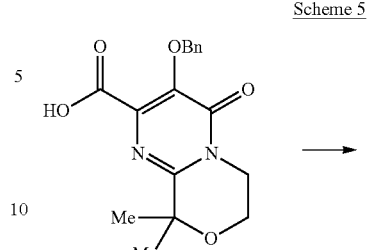
Scheme 5
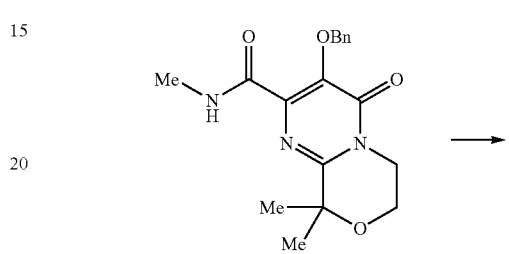
Scheme 4
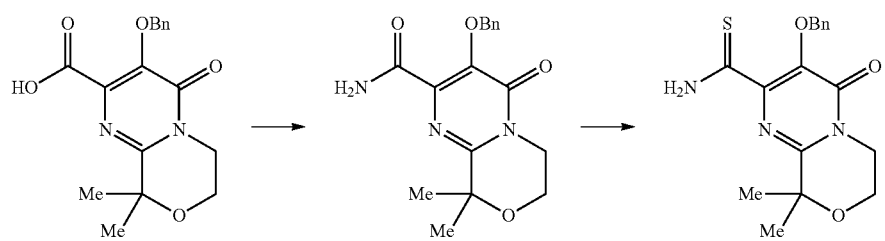
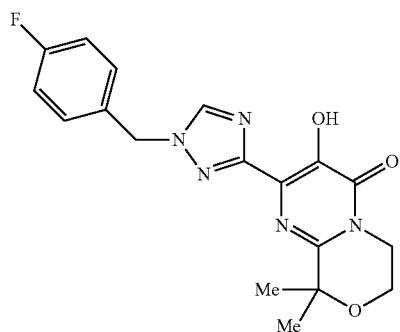
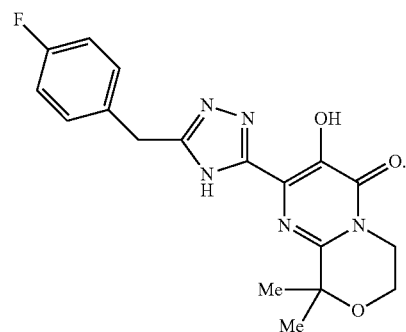

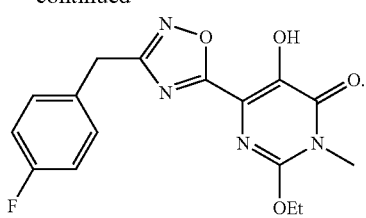
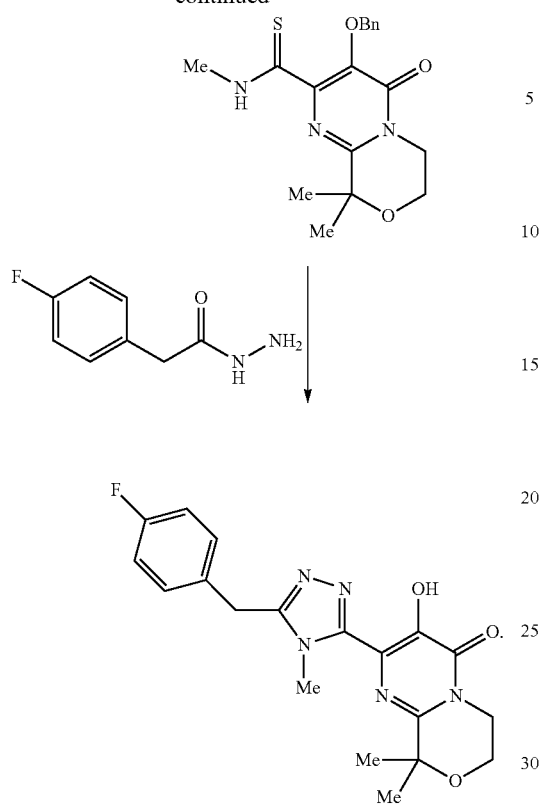
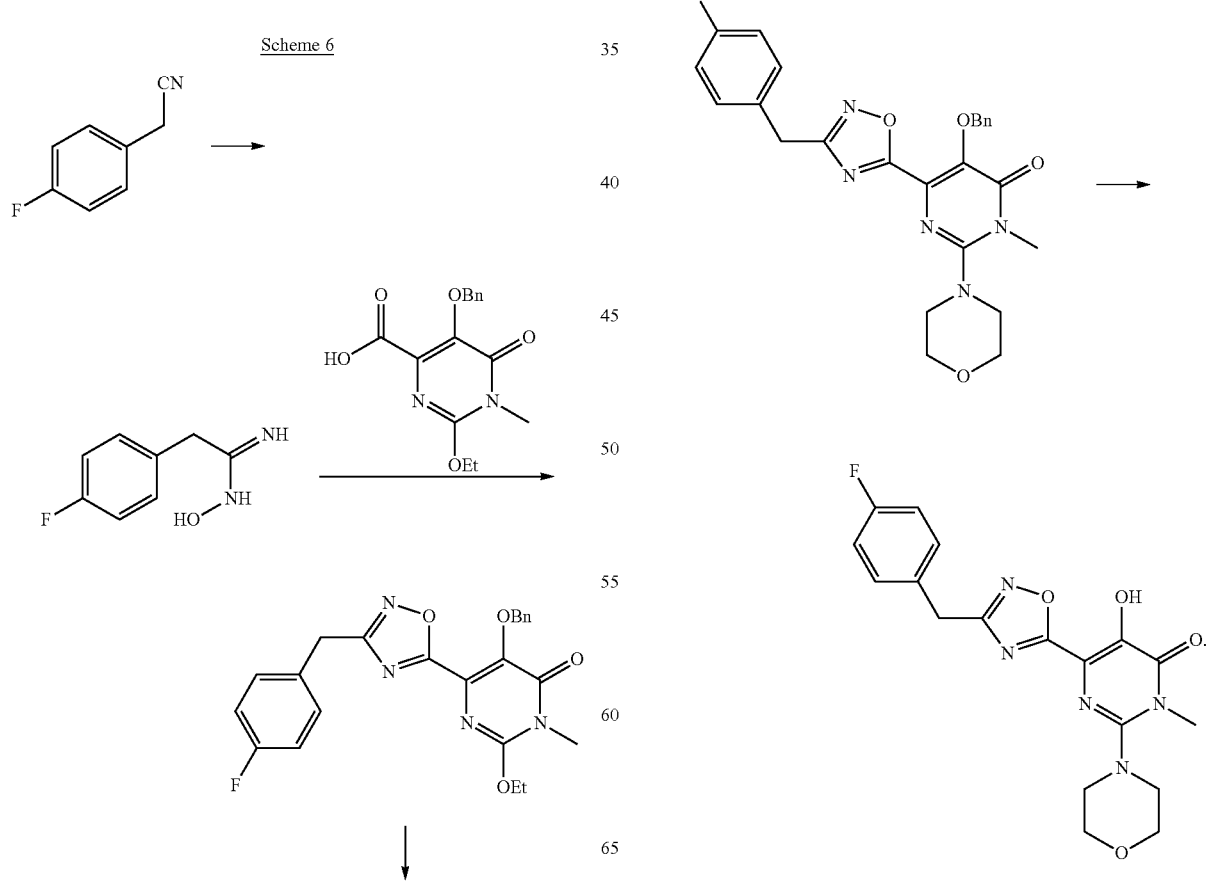

Scheme 8

Scheme 9

Scheme 10

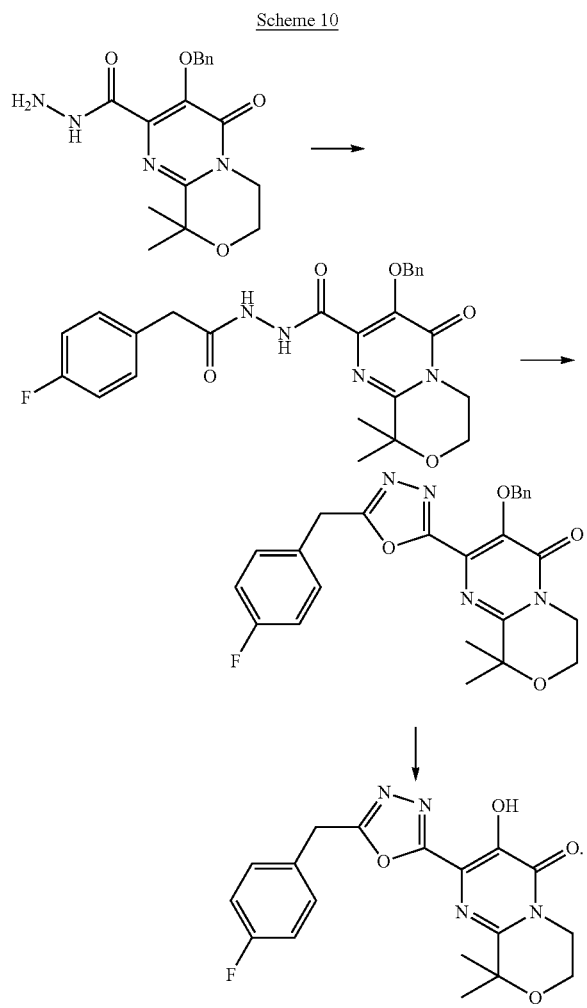

Biological Methods

HIV-Integrase Inhibition Activity. To evaluate in-vitro activity against HIV-integrase, 5 pmole of biotin labeled substrate DNA was bound to 100 µg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994). Results are shown in the Table 1.

TABLE 1

| Example | activity |
|---------|----------|
| 1 | 0.007 |
| 2 | 0.011 |
| 3 | 0.0034 |
| 4 | 0.038 |

TABLE 1-continued

| Example | activity |
|---------|----------|
| 5 | 0.007 |
| 6 | 0.039 |
| 7 | ND |
| 9 | ND |
| 10 | ND |
| 11 | ND |
| 12 | 0.004 |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). the results from at least 2 experiments were used to calculate the $EC_{50}$ values. Results are shown in the Table 2.

TABLE 2

| Example | Activity |
|---------|----------|
| 1 | 0.007 |
| 2 | 0.010 |
| 3 | 0.005 |
| 4 | 0.051 |
| 5 | 0.007 |
| 6 | 0.141 |
| 7 | 31.040 |
| 9 | 22.040 |
| 10 | ND |
| 11 | 0.014 |
| 12 | 0.008 |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently reltegravir, an HIV integrase inhibitor, has been approved by the FDA for treating AIDS and HIV infection.

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

Intermediate 1

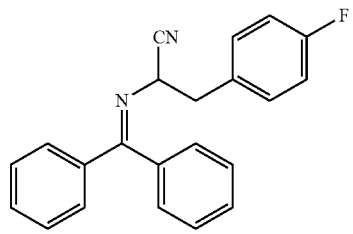 [SMILES: N#CC(Cc1ccc(F)cc1)N=C(c1ccccc1)c1ccccc1]

2-(Diphenylmethyleneamino)-3-(4-fluorophenyl)propanenitrile (procedure adapted from *J. Org. Chem.* 2003, 68, 50-54). To a solution of 2-(diphenylmethyleneamino)acetonitrile (1.21 g, 5.47 mmol, 1.0 equiv) in CH$_2$Cl$_2$ (9.12 mL) was added 4-fluorobenzyl bromide (0.75 mL, 6.02 mmol, 1.1 equiv), benzyltrimethylammonium chloride (0.10 g, 0.547 mmol, 0.1 equiv), and NaOH (0.99 mL of a 10 M aqueous solution, 9.85 mmol, 1.8 equiv). The reaction was stirred vigorously for 18 h, at which time TLC analysis indicated complete consumption of the starting nitrile. The reaction was added to water and extracted with CH$_2$Cl$_2$ (×3). The combined CH$_2$Cl$_2$ extracts were dried (Na$_2$SO$_4$) and concentrated in vacuo. The crude product was purified by silica gel chromatography (5-30% ethyl acetate/hexane) to provide the title compound (1.65 g, 92% yield) as a viscous yellow oil. $^1$H NMR (400 MHz, CDCl$_3$) δ ppm 7.54-7.65 (m, 2H), 7.38-7.48 (m, 4H), 7.31-7.38 (m, 2H), 7.00-7.09 (m, 2H), 6.89-6.97 (m, 2H), 6.84 (d, J=6.30 Hz, 2H), 4.35 (dd, J=7.81, 6.04 Hz, 1H), 3.10-3.29 (m, 2H); LCMS (ES+, (M+H)$^+$) m/z 329.25.

Intermediate 2

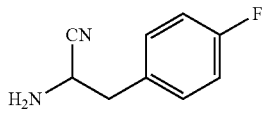

2-Amino-3-(4-fluorophenyl)propanenitrile hydrochloride. To a solution of 2-(diphenylmethyleneamino)-3-(4-fluorophenyl)propanenitrile (1.65 g, 5.02 mmol, 1.0 equiv) in THF (20.1 mL) was added HCl (5.53 mL of a 1 M aqueous solution, 5.53 mmol, 1.1 equiv). After stirring 3 h, the reaction was poured into water and washed with ether (×3). The aqueous layer was neutralized by the addition of 10 M NaOH and extracted with CH$_2$Cl$_2$ (×3). The combined CH$_2$Cl$_2$ extracts were dried (Na$_2$SO$_4$) and then concentrated in vacuo to provide the title compound (0.77 g, 93% yield) as a colorless oil. For convenience, the amine could be converted into the hydrochloride salt by dissolution in ether, treating with 2 M HCl in ether, and filtering the resulting white solid: $^1$H NMR (400 MHz, CDCl$_3$) δ ppm 7.24-7.29 (m, 2H), 7.01-7.08 (m, 2H), 3.85-3.96 (m, 1H), 2.92-3.07 (m, 2H), 1.60 (d, J=7.55 Hz, 2H).

Intermediate 3

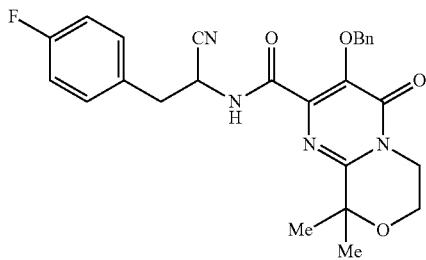 [SMILES: CC1(C)OCCn2c1nc(C(=O)NC(C#N)Cc1ccc(F)cc1)c(OCc1ccccc1)c2=O]

3-(Benzyloxy)-N-(1-cyano-2-(4-fluorophenyl)ethyl)-9,9-dimethyl-4-oxo-4,6,7,9-tetrahydropyrimido[2,1-c][1,4]oxazine-2-carboxamide. To a slurry of 3-(Benzyloxy)-9,9-dimethyl-4-oxo-4,6,7,9-tetrahydropyrimido[2,1-c][1,4]oxazine-2-carboxylic acid (0.80 g, 2.42 mmol, 1.0 equiv) in CH$_2$Cl$_2$ (12 mL) was added DMF (1 drop) followed by oxalyl chloride (0.34 mL, 3.87 mmol, 1.6 equiv). Gas evolution occurred. After stirring 1.5 h, the reaction was concentrated under a stream of nitrogen to provide the acid chloride as a white solid. The acid chloride was then taken up in CH$_2$Cl$_2$ (10 mL) and added slowly to a solution of the hydrochloride salt of 2-amino-3-(4-fluorophenyl)propanenitrile hydrochloride (0.58 g, 2.91 mmol, 1.2 equiv) and triethylamine (1.35 mL, 9.69 mmol, 4 equiv) in CH$_2$Cl$_2$ (10 mL). After stirring 1 h, the reaction was poured into a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. The crude product was purified by silica gel chromatography (10-70% ethyl acetate/hexane) to provide the title compound (1.20 g, ~100% yield) as a viscous colorless oil that foamed under high vacuum. $^1$H NMR (400 MHz, CDCl$_3$) δ ppm 7.70 (d, J=8.81 Hz, 1H), 7.48-7.54 (m, 2H), 7.30-7.40 (m, 3H), 7.20-7.25 (m, 2H), 6.98-7.07 (m, 2H), 5.28-5.36 (m, 2H), 5.19-5.27 (m, 1H), 3.95-4.06 (m, 4H), 3.04-3.12 (m, 1H), 2.94-3.01 (m, 1H), 1.57 (s, 3H), 1.54 (s, 3H); LCMS (ES+, (M+H)$^+$) m/z 477.25.

Intermediate 4

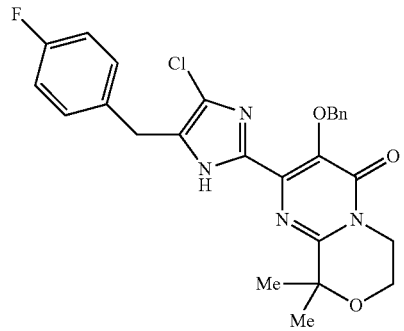 [SMILES: CC1(C)OCCn2c1nc(-c1nc(Cl)c(Cc3ccc(F)cc3)[nH]1)c(OCc1ccccc1)c2=O]

3-(Benzyloxy)-2-(4-chloro-5-(4-fluorobenzyl)-1H-imidazol-2-yl)-9,9-dimethyl-6,7-dihydropyrimido[2,1-c][1,4]oxazin-4(9H)-one. (procedure adapted from *Org. Lett.* 2004, 6, 629-631). To a solution of 3-(benzyloxy)-N-(1-cyano-2-(4-fluorophenyl)ethyl)-9,9-dimethyl-4-oxo-4,6,7,9-tetrahydropyrimido[2,1-c][1,4]oxazine-2-carboxamide (0.48 g, 1.01 mmol, 1.0 equiv) and CCl$_4$ (0.24 mL, 2.52 mmol, 2.5 equiv) in acetonitrile (10 mL) under a nitrogen atmosphere, was added PPh$_3$ (0.39 g, 2.52 mmol, 2.5 equiv). The reaction was heated to 45° C. (oil bath). After stirring 18 h, the reaction was cooled to ambient temperature and concentrated in vacuo. The residue was treated with CH$_2$Cl$_2$ (10 mL) and 0.5 M NaOH (20 mL) and stirred vigorously. After stirring 4 h, the mixture was poured into water and extracted with CH$_2$Cl$_2$ (×3). The combined CH$_2$Cl$_2$ extracts were dried (Na$_2$SO$_4$) and concentrated in vacuo. The crude product was purified by silica gel chromatography (20-80% ethyl acetate/hexane) to provide a viscous yellow oil. This oil was taken up in ether and seeded with a crystal of previously isolated material. After crystallization, the solid was filtered to provide the title compound (0.32 g, 64% yield) as an off-white solid. $^1$H NMR (400 MHz, CDCl$_3$) δ ppm 10.17 (s, 1H), 7.28-7.41 (m, 5H), 6.91-6.96 (m, 4H), 5.27 (s, 2H), 3.95-4.11 (m, 4H), 3.77 (s, 2H), 1.67 (s, 6H); LCMS (ES+, (M+H)$^+$) m/z 495.14.

Intermediate 5

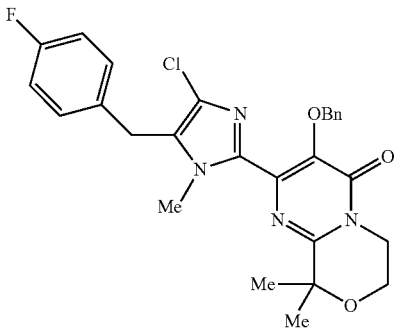 [SMILES: Cn1c(-c2nc3n(c(=O)c2OCc2ccccc2)CCOC3(C)C)nc(Cl)c1Cc1ccc(F)cc1]

3-(Benzyloxy)-2-(4-chloro-5-(4-fluorobenzyl)-1-methyl-1H-imidazol-2-yl)-3-hydroxy-9,9-dimethyl-6,7-dihydropyrimido[2,1-c][1,4]oxazin-4(9H)-one. To a solution of 3-(benzyloxy)-2-(4-chloro-5-(4-fluorobenzyl)-1H-imidazol-2-yl)-9,9-dimethyl-6,7-dihydropyrimido[2,1-c][1,4]oxazin-4 (9H)-one (0.03 g, 0.061 mmol, 1.0 equiv) in THF (0.6 mL), was added NaH (3 mg of a 60% suspension in mineral oil, 0.073 mmol, 1.2 equiv). Gas evolution observed. After stirring 10 min, MeI (0.005 mL, 0.085 mmol, 1.4 equiv) was added. After stirring 2.5 h, LCMS analysis indicated complete alkylation. The reaction was poured into saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. LCMS analysis of the crude product indicated ~2:1 regioselectivity for the alkylation. The crude product was purified by reverse phase preparatory HPLC to provide the title compound (0.021 g, 68% yield) as a viscous pale yellow oil. Regiochemistry verified through observation of an nOe from the N-Me group at δ 3.22 to the benzylic CH$_2$ at δ 3.92: $^1$H NMR (400 MHz, CDCl$_3$) δ ppm 7.18-7.25 (m, 5H), 7.07-7.13 (m, 2H), 6.93-7.01 (m, 2H), 5.14 (s, 2H), 4.04 (s, 4H), 3.92 (s, 2H), 3.22 (s, 3H), 1.57 (s, 6H); LCMS (ES+, (M+H)$^+$) m/z 509.18.

Intermediate 6

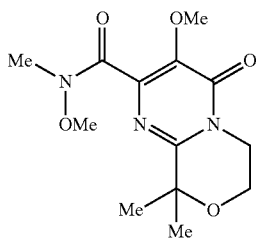 [SMILES: COc1c(C(=O)N(C)OC)nc2n(c1=O)CCOC2(C)C]

N,3-Dimethoxy-N,9,9-trimethyl-4-oxo-4,6,7,9-tetrahydropyrimido[2,1-c][1,4]oxazine-2-carboxamide. To a slurry of 3-methoxy-9,9-dimethyl-4-oxo-4,6,7,9-tetrahydropyrimido[2,1-c][1,4]oxazine-2-carboxylic acid (0.70 g, 2.75 mmol, 1.0 equiv) in CH$_2$Cl$_2$ (9 mL) was added DMF (1 drop) followed by oxalyl chloride (0.34 mL, 3.85 mmol, 1.4 equiv). Gas evolution observed. After stirring 1 h, the reaction was concentrated under a stream of nitrogen to provide the acid chloride as a white solid. The acid chloride was then taken up in CH$_2$Cl$_2$ (10 mL) and added slowly to a solution of the N,O-dimethylhydroxylamine hydrochloride (0.322 g, 3.30 mmol, 1.2 equiv) and triethylamine (1.15 mL, 8.26 mmol, 3 equiv) in CH$_2$Cl$_2$ (10 mL). After stirring 30 min, the reaction was poured into saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. The crude product was purified by silica gel chromatography (30-100% ethyl acetate/hexane) to provide the title compound (0.81 g, 99% yield) as a viscous colorless oil. $^1$H NMR (400 MHz, CDCl$_3$) δ ppm 3.96-4.07 (m, 4H), 3.93 (s, 3H), 3.64 (s, 3H), 3.34 (s, 3H), 1.60 (s, 6H); LCMS (ES+, (M+H)$^+$) m/z 298.25.

Intermediate 7

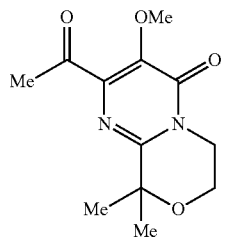 [SMILES: COc1c(C(C)=O)nc2n(c1=O)CCOC2(C)C]

2-Acetyl-3-methoxy-9,9-dimethyl-6,7-dihydropyrimido [2,1-c][1,4]oxazin-4(9H)-one. To a solution of N,3-dimethoxy-N,9,9-trimethyl-4-oxo-4,6,7,9-tetrahydropyrimido[2,1-c][1,4]oxazine-2-carboxamide (0.40 g, 1.35 mmol, 1.0 equiv) in THF (13 mL) at 0° C. (ice/water bath) under a nitrogen atmosphere, was added CH$_3$MgBr (0.63 mL of a 3 M solution in ether, 1.88 mmol, 1.4 equiv). After stirring 3 h, the reaction was cautiously quenched by addition of 1N HCl (10 mL). After stirring 1 h, the reaction was poured into water and extracted with CH$_2$Cl$_2$ (×5). The combined CH$_2$Cl$_2$ extracts were dried (Na$_2$SO$_4$) and then concentrated in vacuo. The crude product was purified by silica gel chromatography (20-100% ethyl acetate/hexane) to provide the title compound (0.054 g, 16% yield) as a white solid. $^1$H NMR (400 MHz, CDCl$_3$) δ ppm 3.98 (s, 3H), 3.96-4.05 (m, 4H), 2.52 (s, 3H), 1.61 (s, 6H); LCMS (ES+, (M+H)$^+$) m/z 253.23.

Intermediate 8

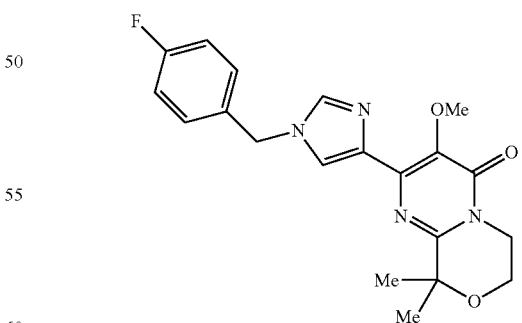

2-(1-(4-Fluorobenzyl)-1H-imidazol-4-yl)-3-methoxy-9,9-dimethyl-6,7-dihydropyrimido[2,1-c][1,4]oxazin-4(9H)-one. To a solution of 2-acetyl-3-methoxy-9,9-dimethyl-6,7-dihydropyrimido[2,1-c][1,4]oxazin-4(9H)-one (0.12 g, 0.476 mmol, 1.0 equiv) in THF (4.8 mL) under a nitrogen atmosphere, was added CuBr$_2$ (0.21 g, 0.951 mmol, 2.0 equiv). After stirring 3 h, the reaction was heated to 50° C. (oil bath). After stirring 23 h, the solids were filtered and the filtrate was concentrated in vacuo to provide the crude bromide intermediate ($^1$H NMR (400 MHz, CDCl$_3$) δ ppm 4.44 (s, 2H), 4.03-4.04 (m, 3H), 3.93-4.10 (m, 4H), 1.62 (s, 6H); LCMS (ES+, (M+H)$^+$) m/z 331.12). LCMS analysis indicated ~80% bromide intermediate, ~10% starting material, and ~10% dibromination product. The crude bromide intermediate was taken up in formamide (4.8 mL) under a nitrogen atmosphere and heated to 140° C. (oil bath). After stirring 4 h, LCMS analysis indicated complete conversion to the imidazole. The reaction was cooled to ambient temperature and NaH (49 mg of a 60% suspension in mineral oil, 1.24 mmol, 2.6 equiv) followed by 4-bromobenzyl bromide (0.18 mmol, 1.41 mmol, 3 equiv) were added. After stirring 4 h, the reaction was poured into saturated aqueous NaHCO$_3$ and extracted with CH$_2$Cl$_2$ (×3). The combined CH$_2$Cl$_2$ extracts were dried (Na$_2$SO$_4$) and then concentrated in vacuo. The crude product was purified by reverse phase preparative HPLC followed by silica gel chromatography (elute with 1% triethylamine/ethyl acetate) to provide the title compound (0.042 g, 23% yield) as a viscous pale yellow oil. Regiochemistry was verified through observation of an nOe from the benzylic CH$_2$ at δ 5.14 to both imidazole protons at δ 7.72 and δ 7.66. $^1$H NMR (400 MHz, CDCl$_3$) δ ppm 7.72 (d, J=1.51 Hz, 1H), 7.66 (d, J=1.26 Hz, 1H), 7.14-7.20 (m, 2H), 7.01-7.09 (m, 2H), 5.14 (s, 2H), 3.98-4.06 (m, 4H), 3.92 (s, 3H), 1.68 (s, 6H); LCMS (ES+, (M+H)$^+$) m/z 385.18.

Intermediate 9

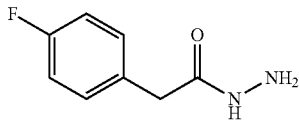 [SMILES: NNC(=O)Cc1ccc(F)cc1]

2-(4-Fluorophenyl)acetohydrazide. To a solution of hydrazine (0.46 mL, 14.49 mmol, 2.5 equiv) in CH$_2$Cl$_2$ (29 mL) was added slowly over 30 sec 2-(4-fluorophenyl)acetyl chloride (0.79 mL, 5.79 mmol, 1.0 equiv). Slight warming of the mixture and white precipitate were observed. After stirring 45 min, the mixture was poured into a saturated aqueous solution of NaHCO$_3$, layered with CH$_2$Cl$_2$ forming a thick emulsion. This emulsion was filtered through a medium glass frit to give a biphasic homogenous solution. This was extracted with CH$_2$Cl$_2$ (×3). The combined CH$_2$Cl$_2$ extracts were dried (Na$_2$SO$_4$) and then concentrated in vacuo to provide the title compound (1.22 g, 124% yield) as a white solid. Source of extra mass is unclear as product is of high purity. Extra mass may reflect a measuring error of the acid chloride. $^1$H NMR (400 MHz, CDCl$_3$) δ ppm 7.19-7.24 (m, 2H), 6.99-7.07 (m, 2H), 6.60 (s, 1H), 3.85 (d, J=2.01 Hz, 2H), 3.52 (s, 2H); LCMS (ES+, (M+H)$^+$) m/z 169.22.

Intermediate 10

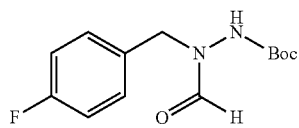 [SMILES: CC(C)(C)OC(=O)NN(C=O)Cc1ccc(F)cc1]

tert-Butyl 2-(4-fluorobenzyl)-2-formylhydrazinecarboxylate. To a solution of tert-butyl 2-(4-fluorobenzyl)hydrazinecarboxylate (0.6 g, 2.50 mmol, 1.0 equiv) in EtOH (2.5 mL) was added ethyl formate (0.81 mL, 9.99 mmol, 4.0 equiv) and the reaction mixture heated to 50° C. (oil bath). After stirring 4 h, the reaction was cooled to ambient temperature and stirred 3 d. The reaction was then heated to 50° C. (oil bath) for 3 h at which time more ethyl formate (1.0 mL, 12.28 mmol, 4.9 equiv) was added. After stirring a further 4 h, the reaction was concentrated in vacuo. The crude product was purified by silica gel chromatography (elute with 10-70% ethyl acetate/hexane) to provide the title compound (0.11 g, 16% yield) as a colorless oil which slowly crystallized. Unreacted tert-butyl 2-(4-fluorobenzyl)hydrazinecarboxylate was recovered from the mother liquor. $^1$H NMR (400 MHz, CDCl$_3$) δ ppm 8.20 (s, 1H), 7.20-7.25 (m, 2H), 7.00-7.08 (m, 2H), 6.27 (s, 1H), 4.58 (s, 2H), 1.43 (s, 9H); LCMS (ES+, (M+H)$^+$) m/z 269.22.

Intermediate 11

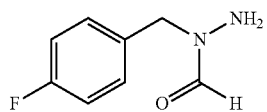

N-(4-Fluorobenzyl)formohydrazide. To a solution of tert-butyl 2-(4-fluorobenzyl)-2-formylhydrazinecarboxylate (0.11 g, 0.410 mmol, 1.0 equiv) in CH$_2$Cl$_2$ (1.02 mL) was added TFA (1.02 mL). Gas evolution was observed. After stirring 30 min, the reaction was poured into a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo to provide the title compound (0.056 g, 81% yield) as a viscous yellow oil. $^1$H NMR (400 MHz, CDCl$_3$) δ ppm (first tautomer) 8.24 (s, 1H), 7.18-7.31 (m, 2H), 7.00-7.14 (m, 2H), 4.47 (s, 2H), 4.11 (s, 2H), (second tautomer) 8.37 (s, 1H), 7.18-7.31 (m, 2H), 7.00-7.13 (m, 2H), 4.62 (s, 2H), 3.63 (s, 2H); LCMS (ES+, (M+H)$^+$) m/z 169.27.

Intermediate 12

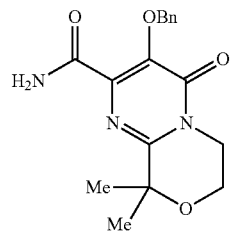 [SMILES: CC1(C)OCCn2c1nc(C(N)=O)c(OCc1ccccc1)c2=O]

3-(Benzyloxy)-9,9-dimethyl-4-oxo-4,6,7,9-tetrahydropyrimido[2,1-c][1,4]oxazine-2-carboxamide. To a slurry of 3-(benzyloxy)-9,9-dimethyl-4-oxo-4,6,7,9-tetrahydropyrimido[2,1-c][1,4]oxazine-2-carboxylic acid (0.60 g, 1.82 mmol, 1.0 equiv) in CH$_2$Cl$_2$ (9 mL) was added DMF (1 drop) followed by oxalyl chloride (0.22 mL, 2.54 mmol, 1.4 equiv). Gas evolution was observed. After stirring 1 h, the reaction was concentrated under a stream of nitrogen to provide the acid chloride as a white solid. The acid chloride was taken up in CH$_2$Cl$_2$ (5 mL) and added dropwise to NH$_4$OH (10 mL).

After stirring 1 h, the reaction was poured into a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo to provide the title compound (0.54 g, 90% yield) as a white solid. $^1$H NMR (400 MHz, CDCl$_3$) δ ppm 7.50-7.60 (m, 2H), 7.28-7.40 (m, 3H), 7.21 (s, 1H), 5.64 (s, 1H), 5.32 (s, 2H), 3.95-4.09 (m, 4H), 1.62 (s, 5H); LCMS (ES+, (M+H)$^+$) m/z 330.22.

Intermediate 13

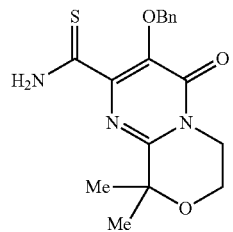

3-(Benzyloxy)-9,9-dimethyl-4-oxo-4,6,7,9-tetrahydropyrimido[2,1-c][1,4]oxazine-2-carbothioamide. To a solution of 3-(benzyloxy)-9,9-dimethyl-4-oxo-4,6,7,9-tetrahydropyrimido[2,1-c][1,4]oxazine-2-carboxamide (0.54 g, 1.64 mmol, 1.0 equiv) in THF (33 mL) under a nitrogen atmosphere, was added Lawesson's reagent (0.40 g, 0.98 mmol, 0.6 equiv). The yellow solution was then heated to 70° C. (oil bath). After stirring for 1 h, the reaction was cooled to ambient temperature and concentrated in vacuo. The crude product was purified by silica gel chromatography (30-100% ethyl acetate/hexane) to provide the title compound (0.28 g, 49% yield) as a pale yellow solid. $^1$H NMR (400 MHz, CDCl$_3$) δ ppm 8.04 (s, 1H), 7.63 (s, 1H), 7.50-7.57 (m, 2H), 7.27-7.41 (m, 3H), 5.30 (s, 2H), 3.96-4.08 (m, 4H), 1.62 (s, 6H); LCMS (ES+, (M+H)$^+$) m/z 346.17.

Intermediate 14

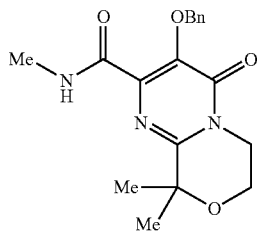 [SMILES: CNC(=O)c1nc2n(c(=O)c1OCc1ccccc1)CCOC2(C)C]

3-(Benzyloxy)-N,9,9-trimethyl-4-oxo-4,6,7,9-tetrahydropyrimido[2,1-c][1,4]oxazine-2-carboxamide. To a slurry of 3-(benzyloxy)-9,9-dimethyl-4-oxo-4,6,7,9-tetrahydropyrimido[2,1-c][1,4]oxazine-2-carboxamide (0.40 g, 1.21 mmol, 1.0 equiv) in CH$_2$Cl$_2$ (4 mL) was added DMF (1 drop) followed by oxalyl chloride (0.15 mL, 1.70 mmol, 1.4 equiv). Gas evolution was observed. After stirring 2 h, the reaction was concentrated under a stream of nitrogen to provide the acid chloride as a white solid. The acid chloride was taken up in CH$_2$Cl$_2$ (4 mL) and added slowly to a solution of MeNH$_2$ (2.42 mL of a 2 M solution in MeOH, 4.84 mmol, 4 equiv) in CH$_2$Cl$_2$ (3 mL). After stirring 30 min, the reaction was poured into a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo to provide the title compound (0.41 g, 99% yield) as a white solid. $^1$H NMR (400 MHz, CDCl$_3$) δ ppm 7.54-7.60 (m, 2H), 7.28-7.40 (m, 3H), 5.27 (s, 2H), 3.97-4.07 (m, 4H), 2.92 (d, J=5.04 Hz, 3H), 1.62 (s, 6H); LCMS (ES+, (M+H)$^+$) m/z 344.

Intermediate 15

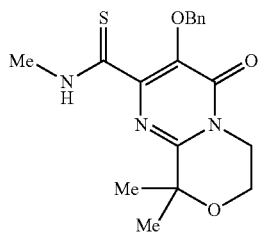

3-(Benzyloxy)-N,9,9-trimethyl-4-oxo-4,6,7,9-tetrahydropyrimido[2,1-c][1,4]oxazine-2-carbothioamide. To a solution of 3-(benzyloxy)-N,9,9-trimethyl-4-oxo-4,6,7,9-tetrahydropyrimido[2,1-c][1,4]oxazine-2-carboxamide (0.40 g, 1.17 mmol, 1.0 equiv) in THF (12 mL) under a nitrogen atmosphere, was added Lawesson's reagent (0.28 g, 0.70 mmol, 0.6 equiv). The yellow solution was then heated to 50° C. (oil bath). After stirring for 1 h, the reaction was cooled to ambient temperature and concentrated in vacuo. The crude product was purified by silica gel chromatography (20-100% ethyl acetate/hexane) to provide the title compound (0.38 g, 90% yield) as a yellow solid. $^1$H NMR (400 MHz, CDCl$_3$) δ ppm 8.19 (s, 1H), 7.45-7.57 (m, 2H), 7.29-7.42 (m, 3H), 5.25 (s, 2H), 3.93-4.12 (m, 4H), 3.17 (d, J=5.04 Hz, 3H), 1.62 (s, 6H); LCMS (ES+, (M+H)$^+$) m/z 360.19.

Intermediate 16

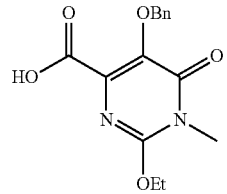 [SMILES: CCOc1nc(C(=O)O)c(OCc2ccccc2)c(=O)n1C]

5-(Benzyloxy)-2-ethoxy-1-methyl-6-oxo-1,6-dihydropyrimidine-4-carboxylic acid. To a stirred solution of LiOH.H$_2$O (1.26 g, 30 mmol) in EtOH (100 mL) at 40° C. was added ethyl 5-(benzyloxy)-1-methyl-2-(methylthio)-6-oxo-1,6-dihydropyrimidine-4-carboxylate (prepared according to the procedure in WO2004062613) (6.7 g, 20 mmol). The resulting reaction mixture was stirred at room temperature for 5 h then concentrated. The residue was taken up in aq. HCl (50 mL) and extracted with EtOAc (2×100 mL). The combined organic fractions were dried (Na$_2$SO$_4$), filtered and concentrated to give the desired product (6 g, 99% yield) as off-white solid which was used in the next step without purification.

Intermediate 17

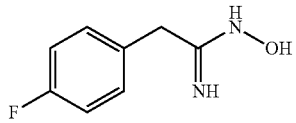 [SMILES: N=C(Cc1ccc(F)cc1)NO]

2-(4-Fluorophenyl)-N-hydroxyacetimidamide. A solution of 2-(4-fluorophenyl)acetonitrile (1.35 g, 10 mmol) and 50% aq. hydroxylamine (1.33 g, 20 mmol) in EtOH (10 mL) was stirred at 90° C. for 18 h then cooled and concentrated to afford the title compound (1.68 g, 100% yield) as white solid. $^1$HNMR (500 MHz, CDCl$_3$) δ: 8.04-7.85 (1H, br s), 7.24 (2H, dd, J=8.6, 5.5 Hz), 7.01 (2H, t, J=8.6 Hz), 4.46 (2H, s), 3.43 (2H, s). LCMS (M+H): 169.14.

Intermediate 18

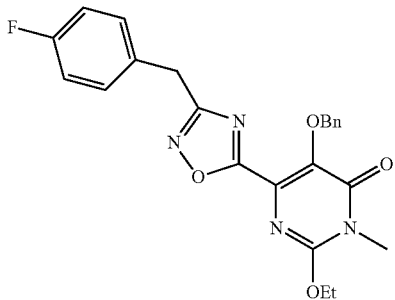 [SMILES: CCOc1nc(-c2nc(Cc3ccc(F)cc3)no2)c(OCc2ccccc2)c(=O)n1C]

5-(Benzyloxy)-2-ethoxy-6-(3-(4-fluorobenzyl)-1,2,4-oxadiazol-5-yl)-3-methylpyrimidin-4(3H)-one. A mixture of 5-(benzyloxy)-2-ethoxy-1-methyl-6-oxo-1,6-dihydropyrimidine-4-carboxylic acid (0.5045 g, 3 mmol), 2-(4-fluorophenyl)-N-hydroxyacetimidamide (0.9190, 3.02 mmol), HATU (1.255 g, 3.3 mmol) and DIEA (0.5 mL) in 1,4-dioxane (20 mL) was heated at 100° C. for 6 h. The mixture was cooled, diluted with EtOAc (50 mL), washed with water (10 mL), sat. NaHCO$_3$ (10 mL), brine (10 mL), then dried (Na$_2$SO$_4$), filtered and concentrated to give a brown residue. This residue was purified by flash chromatography on a silica gel column using 7:3 Hexanes/EtOAc as eluant to afford the title compound product (0.68 g, 52% yield) as a yellow solid. $^1$HNMR (500 MHz, CDCl$_3$) δ: 7.41-7.38 (2H, m), 7.30 (2H, dd, J=8.6, 5.2 Hz), 7.27-7.24 (3H, m), 6.99 (2H, t, J=8.6 Hz), 5.24 (2H, s), 4.52 (2H, q, J=7.0 Hz), 4.13 (2H, s), 3.47 (3H, s), 1.44 (3H, t, J=7.0 Hz). HRMS (M+H) calcd for C$_{23}$H$_{22}$N$_4$O$_4$F: 437.1625. found: 437.4719. Anal calcd for C$_{23}$H$_{21}$N$_4$O$_4$F: C, 63.29; H, 4.85; N, 12.83. found: C, 62.76; H, 4.84; N, 12.81.

Intermediate 19

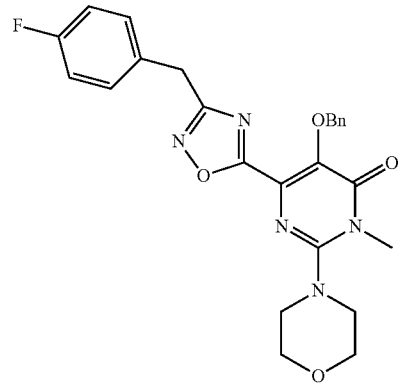 [SMILES: Cn1c(N2CCOCC2)nc(-c2nc(Cc3ccc(F)cc3)no2)c(OCc2ccccc2)c1=O]

5-(Benzyloxy)-6-(3-(4-fluorobenzyl)-1,2,4-oxadiazol-5-yl)-3-methyl-2-morpholinopyrimidin-4(3H)-one. A mixture of 5-(benzyloxy)-1-methyl-2-morpholino-6-oxo-1,6-dihydropyrimidine-4-carboxylic acid (prepared according to the procedure in WO2004062613 (0.35 g, 1 mmol), 2-(4-fluorophenyl)-N-hydroxyacetimidamide (0.25, 1.5 mmol) HATU (0.76 g, 2 mmol), DIEA (0.35 mL) and DMAP (10 mg) in 1,4-dioxane (5 mL) was heated at 110° C. for 5 h. The mixture was cooled, diluted with Et$_2$O (50 mL), washed with water (10 mL), sat. NaHCO$_3$ (10 mL), brine (10 mL) then dried (Na$_2$SO$_4$), filtered and concentrated to give a brown residue. This residue was purified by flash chromatography on a silica gel column using 1:1 hexanes/EtOAc as eluant to afford the title compound (0.24 g, 50% yield) as a white solid. $^1$HNMR (500 MHz, CDCl$_3$) δ: 7.42-7.39 (2H, m), 7.32 (2H, dd, J=8.4, 5.4 Hz), 7.28-7.25 (3H, m), 7.00 (2H, t, J=8.6 Hz), 5.28 (2H, s), 4.14 (2H, s), 3.84-3.82 (4H, m), 3.55 (3H, s), 3.24-3.22 (4H, m). HRMS (M+H) calcd for C$_{25}$H$_{25}$N$_5$O$_4$F: 478.1491. found: 478.5663.

Intermediate 20

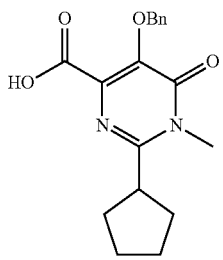 [SMILES: Cn1c(C2CCCC2)nc(C(=O)O)c(OCc2ccccc2)c1=O]

5-(Benzyloxy)-2-cyclopentyl-1-methyl-6-oxo-1,6-dihydropyrimidine-4-carboxylic acid. A mixture of ethyl 5-(benzyloxy)-2-cyclopentyl-1-methyl-6-oxo-1,6-dihydropyrimidine-4-carboxylate (prepared according to the procedure in Naidu, B. N. Synlett, 2008;) (1.1 g, 3.1 mmol) and LiOH.H$_2$O (0.25 g, 6 mmol) in 2:1 THF/H$_2$O (15 mL) was heated at 80° C. for 1 h then cooled. The reaction mixture concentrated and the residue acidified with 1 N aq. HCl and the resulting solid isolated by filtration to yield the title compound (0.98 g, 97% yield) as a white solid. $^1$HNMR (500 MHz, CDCl$_3$) δ: 7.56-7.52 (2H, m), 7.36-7.28 (3H, m), 5.42 (2H, s), 3.59 (3H, s), 3.20-3.14 (1H, m), 2.08-2.01 (2H, m), 1.93-1.78 (4H, m), 1.74-1.67 (2H, m). HRMS (M+H) calcd for $C_{18}H_{21}N_2O_4$: 329.1501. found: 329.1489.

Intermediate 21

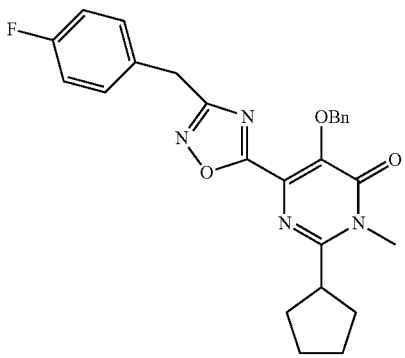 [SMILES: Cn1c(C2CCCC2)nc(-c2nc(Cc3ccc(F)cc3)no2)c(OCc2ccccc2)c1=O]

5-(Benzyloxy)-2-cyclopentyl-6-(3-(4-fluorobenzyl)-1,2,4-oxadiazol-5-yl)-3-methylpyrimidin-4(3H)-one. To a stirred solution of 5-(benzyloxy)-2-cyclopentyl-1-methyl-6-oxo-1,6-dihydropyrimidine-4-carboxylic acid (0.33, 1 mmol) in $CH_2Cl_2$ (3 mL) was added a catalytic amount of DMF followed by 3 mL of a 2M solution of oxalyl chloride dissolved in $CH_2Cl_2$. The resulting yellow reaction mixture was stirred for 1 h and concentrated to give a yellow oil. The yellow oil was dissolved in 1,4-dioxane (9 mL) and added to a stirred solution of 2-(4-fluorophenyl)-N-hydroxyacetimidamide (0.18 g, 1.1 mmol) and DIEA (0.2 mL) in 1,4-dioxane (1 mL). After 4 h at room temperature, the reaction mixture was heated at 90° C. for 14 h. The mixture was cooled to room temperature and purified by flash column chromatography on a silica gel column using 7:1 hexanes/EtOAc as eluant to afford the title compound (0.29 g, 63% yield) as an off-white solid. $^1$HNMR (500 MHz, CDCl$_3$) δ: 7.43-7.39 (2H, m), 7.33 (2H, dd, J=8.6, 5.2 Hz), 7.28-7.23 (3H, m), 7.00 (2H, t, J=8.6 Hz), 5.34 (2H, s), 4.14 (2H, s), 3.63 (3H, s), 3.21-3.14 (1H, m), 2.05-1.99 (4H, m), 1.88-1.80 (2H, m), 1.71-1.62 (2H, m). HRMS (M+H) calcd for $C_{26}H_{26}N_4O_3F$: 461.1989. found: 461.1979.

Intermediate 22

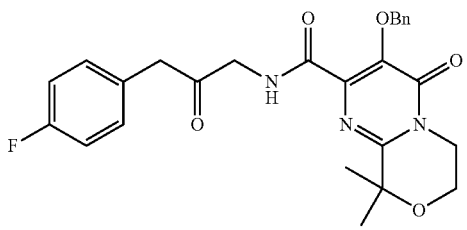 [SMILES: CC1(C)OCCn2c1nc(C(=O)NCC(=O)Cc1ccc(F)cc1)c(OCc1ccccc1)c2=O]

3-(Benzyloxy)-N-(3-(4-fluorophenyl)-2-oxopropyl)-9,9-dimethyl-4-oxo-4,6,7,9-tetrahydropyrimido[2,1-c][1,4]oxazine-2-carboxamide. A mixture of 3-(benzyloxy)-9,9-dimethyl-4-oxo-4,6,7,9-tetrahydropyrimido[2,1-c][1,4]oxazine-2-carboxylic acid (prepared according to the procedure in Naidu, B. N. et al WO2005118593) (0.495 g, 1.5 mmol), 1-amino-3-(4-fluorophenyl)propan-2-one hydrochloride (prepared according to the procedure in Maeda, S. et al Chem. Pharm. Bull. 1984, 32, 2536-2543; 0.406 g, 2 mmol), HATU (0.760 g, 2 mmol), Et$_3$N (0.56 mL, 4 mmol) and DMAP (60 mg) in DMF (15 mL) was stirred at room temperature. After 4 h, the reaction mixture was diluted with Et$_2$O (100 mL), washed with water (3×10 mL), brine (10 mL), dried (Na$_2$SO$_4$), filtered and concentrated to give the title compound (0.57 g, 78% yield) as a viscous yellow oil which was used in the subsequent step without purification. $^1$HNMR (500 MHz, CDCl$_3$) δ: 8.10-8.07 (1H, br s), 7.56 (2H, d, J=7.3 Hz), 7.34-7.28 (3H, m), 7.19 (2H, dd, J=8.6, 5.5 Hz), 7.03 (2H, t, J=8.6 Hz), 5.29 (2H, s), 4.30 (2H, d, J=4.9 Hz), 4.04-3.98 (4H, m), 3.75 (2H, s), 2.79 (6H, s), 1.62 (6H, s). HRMS (M+H) calcd for $C_{26}H_{27}N_3O_5F$: 480.1935. found: 480.1930.

Intermediate 23

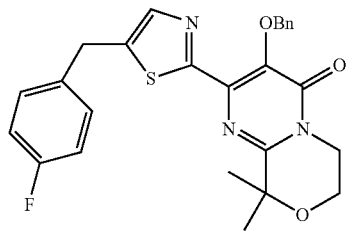 [SMILES: CC1(C)OCCn2c1nc(-c1ncc(Cc3ccc(F)cc3)s1)c(OCc1ccccc1)c2=O]

3-(Benzyloxy)-2-(5-(4-fluorobenzyl)thiazol-2-yl)-9,9-dimethyl-6,7-dihydropyrimido[2,1-c][1,4]oxazin-4(9H)-one. A solution of 3-(benzyloxy)-N-(3-(4-fluorophenyl)-2-oxopropyl)-9,9-dimethyl-4-oxo-4,6,7,9-tetrahydropyrimido[2,1-c][1,4]oxazine-2-carboxamide: (0.12 g, 0.25 mmol) and Lawesson's reagent (0.11 g, 0.275 mmol) in toluene (10 mL) was stirred 15 min at room temperature, 30 min at 60° C. and 2 h at 100° C. The mixture was cooled, concentrated and purified by preparative HPLC on a C18 column using water/MeOH containing 0.1% TFA as eluent to afford the title compound (0.05 g, 43% yield) as a yellow solid. $^1$HNMR (500 MHz, CDCl$_3$) δ: 7.78 (1H, s), 7.54-7.51 (2H, m), 7.32-7.29 (3H, m), 7.19 (2H, dd, J=8.6, 5.2 Hz), 7.01 (2H, t, J=8.6 Hz), 5.35 (2H, s), 4.15 (2H, s), 4.06-4.00 (4H, m), 1.66 (6H, s). HRMS (M+H) calcd for $C_{26}H_{25}N_3O_3FS$: 478.1601. found: 478.1623.

Intermediate 24

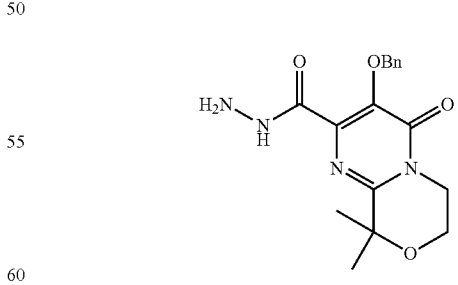

3-(Benzyloxy)-9,9-dimethyl-4-oxo-4,6,7,9-tetrahydropyrimido[2,1-c][1,4]oxazine-2-carbohydrazide. To a stirred suspension of 3-(benzyloxy)-9,9-dimethyl-4-oxo-4,6,7,9-tetrahydropyrimido[2,1-c][1,4]oxazine-2-carboxylic acid (prepared according to the procedure in Naidu, B. N. et al WO2005118593) (0.66 g, 2 mmol) in CH$_2$Cl$_2$ (10 mL) containing catalytic DMF was added oxalyl chloride in CH$_2$Cl$_2$ (2 M, 2 mL, 4 mmol) at room temperature. After 3 h, the resulting clear reaction solution was concentrated to remove excess oxalyl chloride. The resulting residue was re-dissolved in CH$_2$Cl$_2$ (20 mL) and treated with anhydrous hydrazine (0.34 mL, 10 mmol). After 2 h at room temperature, the reaction mixture was concentrated and the residue was taken up in EtOAc (100 mL) and washed with sat. NaHCO$_3$ (10 mL), water (10 mL), brine (10 mL) then dried (Na$_2$SO$_4$), filtered and concentrated to give a white solid. This was digested with Et$_2$O (20 mL) and filtered. Concentration of filtrate provided the title compound (0.17 g, 27% yield). $^1$HNMR (500 MHz, CDCl$_3$) δ: 8.35 (1H, s), 7.55 (2H, d, J=7.3 Hz), 7.38-7.31 (3H, m), 5.30 (2H, s), 4.03-3.97 (6H, m), 1.60 (6H, s). HRMS (M+H) calcd for C$_{17}$H$_{21}$N$_4$O$_5$: 345.1563. found: 345.1577.

Intermediate 25

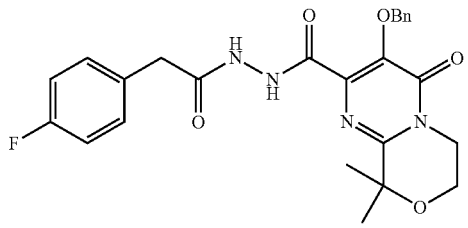 [SMILES: CC1(C)OCCn2c1nc(C(=O)NNC(=O)Cc1ccc(F)cc1)c(OCc1ccccc1)c2=O]

3-(Benzyloxy)-N'-(2-(4-fluorophenyl)acetyl)-9,9-dimethyl-4-oxo-4,6,7,9-tetrahydropyrimido[2,1-c][1,4]oxazine-2-carbohydrazide. To stirred solution of 3-(benzyloxy)-9,9-dimethyl-4-oxo-4,6,7,9-tetrahydropyrimido[2,1-c][1,4]oxazine-2-carbohydrazide (0.170 g, 0.49 mmol) and Et$_3$N (0.14 mL, 1 mmol) in CH$_2$Cl$_2$ (10 mL) was added 2-(4-fluorophenyl)acetyl chloride (69 mL, 0.5 mmol) and the mixture stirred 2 h at room temperature. The reaction mixture was purified by preparative HPLC on a C18 column using water/MeOH containing 0.1% TFA as eluent to afford the title compound (0.078 g, 33% yield) as a white solid. $^1$HNMR (500 MHz, CDCl$_3$) δ: 9.97 (1H, d, J=7.0 Hz), 8.42 (1H, d, J=6.7 Hz), 7.54 (2H, d, J=6.7 Hz), 7.35-7.27 (5H, m), 7.05 (2H, t, J=8.6 Hz), 5.36 (2H, s), 4.04-3.98 (4H, m), 3.64 (2H, s), 1.60 (6H, s). HRMS (M+H) calcd for C$_{25}$H$_{26}$N$_4$O$_5$F: 481.1887. found: 481.1866.

Intermediate 26

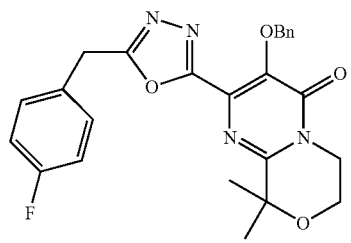 [SMILES: CC1(C)OCCn2c1nc(-c1nnc(Cc3ccc(F)cc3)o1)c(OCc1ccccc1)c2=O]

3-(Benzyloxy)-2-(5-(4-fluorobenzyl)-1,3,4-oxadiazol-2-yl)-9,9-dimethyl-6,7-dihydropyrimido[2,1-c][1,4]oxazin-4(9H)-one. To stirred solution of 3-(benzyloxy)-N'-(2-(4-fluorophenyl)acetyl)-9,9-dimethyl-4-oxo-4,6,7,9-tetrahydropyrimido[2,1-c][1,4]oxazine-2-carbohydrazide (0.075 g, 0.16 mmol), Ph$_3$P (0.074 g, 0.28 mmol) and DIEA (0.16 mL, 0.91 mmol) in anhydrous CH$_3$CN (3 mL) was added hexachloroethane (0.048 g, 0.20 mmol) all at once at room temperature. After 4 h, the resulting greenish-yellow reaction mixture was purified by preparative HPLC on a C18 column using water/MeOH containing 0.1% TFA as eluent to afford title compound (0.072 g, 86% yield) as a yellow solid. $^1$HNMR (500 MHz, CDCl$_3$) δ: 7.42-7.40 (2H, m), 7.30-7.28 (3H, m), 7.24 (2H, dd, J=8.2, 5.55.34 (2H, s), 4.20 (2H, s), 4.07-4.01 (4H, m), 1.64 (6H, s). Hz)), 6.99 (2H, t, J=8.6 Hz), HRMS (M+H) calcd for C$_{25}$H$_{24}$N$_4$O$_4$F: 463.1782. found: 463.1788.

Example 1

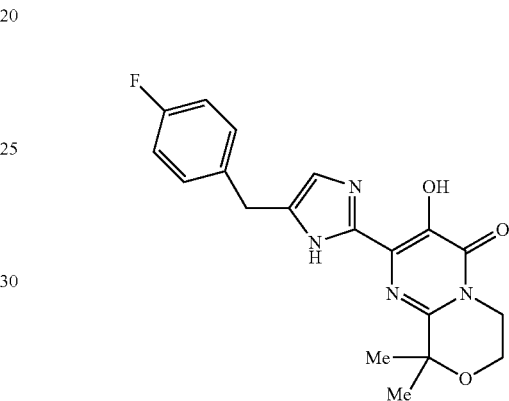

2-(5-(4-Fluorobenzyl)-1H-imidazol-2-yl)-3-hydroxy-9,9-dimethyl-6,7-dihydropyrimido[2,1-c][1,4]oxazin-4(9H)-one. To a solution of 3-(benzyloxy)-2-(4-chloro-5-(4-fluorobenzyl)-1H-imidazol-2-yl)-9,9-dimethyl-6,7-dihydropyrimido[2,1-c][1,4]oxazin-4(9H)-one (0.03 g, 0.061 mmol, 1.0 equiv) in MeOH (3 mL) under a nitrogen atmosphere, was added formic acid (0.1 mL, 2.61 mmol, 43 equiv) and 10% Pd/C (0.065 g, 0.061 mmol, 1.0 equiv). The reaction was stirred for 5 h after which LCMS analysis indicated complete benzyl hydrogenolysis but no chloride reduction. The reaction was warmed to 40° C. (oil bath) and stirred 2 h. LCMS analysis now indicated complete chloride reduction. The reaction was cooled to ambient temperature and stirred a further 16 h. The reaction was then filtered through celite and concentrated in vacuo. The residue was added to saturated aqueous solution of NaHCO$_3$ and extracted with CH$_2$Cl$_2$ (×5). The combined CH$_2$Cl$_2$ extracts were dried (Na$_2$SO$_4$) and then concentrated in vacuo. The crude product was purified by silica gel chromatography (7% MeOH/CH$_2$Cl$_2$) to provide the title compound (0.008 g, 36% yield) as a tan solid. $^1$H NMR (400 MHz, d$_7$-DMF) δ ppm (major imidazole tautomer) 13.14 (s, 1H), 7.48-7.58 (m, 2H), 7.39 (s, 1H), 7.29 (t, J=8.56 Hz, 2H), 4.21-4.25 (m, 2H), 4.15 (s, 2H), 4.08 (t, J=5.16 Hz, 2H), 1.74 (s, 6H); LCMS (ES+, (M+H)$^+$) m/z 371.17.

Example 2

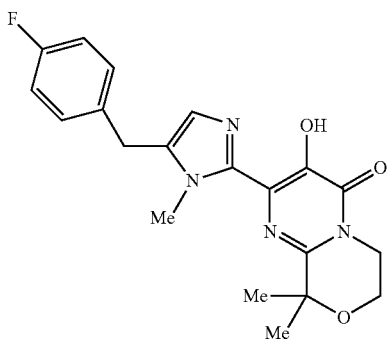 [SMILES: Cn1c(Cc2ccc(F)cc2)cnc1-c1nc2n(c(=O)c1O)CCOC2(C)C]

2-(5-(4-Fluorobenzyl)-1-methyl-1H-imidazol-2-yl)-3-hydroxy-9,9-dimethyl-6,7-dihydropyrimido[2,1-c][1,4]oxazin-4(9H)-one. To a solution of 3-(benzyloxy)-2-(4-chloro-5-(4-fluorobenzyl)-1-methyl-1H-imidazol-2-yl)-3-hydroxy-9,9-dimethyl-6,7-dihydropyrimido[2,1-c][1,4]oxazin-4(9H)-one (0.02 g, 0.039 mmol, 1.0 equiv) in EtOH (1 mL) was added ammonium formate (0.04 g, 0.634 mmol, 16 equiv) and 10% Pd/C (0.04 g, 0.376 mmol, 9.6 equiv). After stirring 4 h, LCMS analysis indicated complete conversion to product. The reaction was then filtered through celite and concentrated in vacuo. The crude product was purified by silica gel chromatography (7% MeOH/CH$_2$Cl$_2$) to provide the title compound (0.008 g, 53% yield) as an off-white solid. $^1$H NMR (400 MHz, CDCl$_3$) δ ppm 7.09-7.19 (m, 2H), 6.97-7.06 (m, J=8.62, 6.48, 2.27 Hz, 2H), 6.90 (s, 1H), 3.99-4.09 (m, 4H), 3.97 (s, 2H), 3.95 (s, 3H), 1.57 (s, 6H); LCMS (ES+, (M+H)$^+$) m/z 385.18.

Example 3

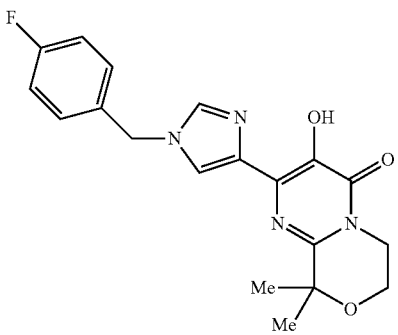 [SMILES: CC1(C)OCCn2c1nc(-c1cn(Cc3ccc(F)cc3)cn1)c(O)c2=O]

2-(1-(4-Fluorobenzyl)-1H-imidazol-4-yl)-3-hydroxy-9,9-dimethyl-6,7-dihydropyrimido[2,1-c][1,4]oxazin-4(9H)-one. To a solution of 2-(1-(4-fluorobenzyl)-1H-imidazol-4-yl)-3-methoxy-9,9-dimethyl-6,7-dihydropyrimido[2,1-c][1,4]oxazin-4(9H)-one (0.042 g, 0.109 mmol, 1.0 equiv) in dichloroethane (1.1 mL) under a nitrogen atmosphere, was added BBr$_3$·SMe$_2$ (0.137 g, 0.437 mmol, 4.0 equiv). The reaction was then heated to 80° C. (oil bath). After stirring 1 h, the reaction was cooled to ambient temperature and cautiously quenched with water (5 mL). The mixture was poured into saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. The crude product was purified by reverse phase preparatory HPLC to provide the title compound (0.017 g, 42% yield) as a pale gray solid. $^1$HNMR (400 MHz, CDCl$_3$) δ ppm 11.34 (s, 1H), 7.59 (d, J=1.01 Hz, 1H), 7.42 (d, J=1.51 Hz, 1H), 7.20 (dd, J=8.69, 5.16 Hz, 2H), 7.05-7.13 (m, 2H), 5.16 (s, 2H), 3.95-4.08 (m, 4H), 1.58 (s, 6H); LCMS (ES+, (M+H)$^+$) m/z 371.24.

Example 4

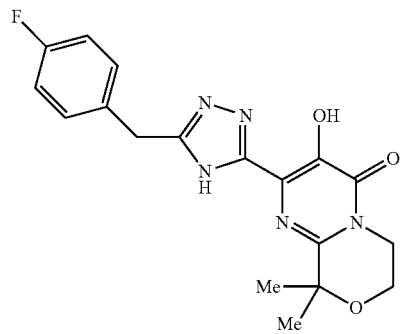 [SMILES: CC1(C)OCCn2c1nc(-c1nnc(Cc3ccc(F)cc3)[nH]1)c(O)c2=O]

2-(5-(4-Fluorobenzyl)-4H-1,2,4-triazol-3-yl)-3-hydroxy-9,9-dimethyl-6,7-dihydropyrimido[2,1-c][1,4]oxazin-4(9H)-one. To a slurry of 3-(benzyloxy)-9,9-dimethyl-4-oxo-4,6,7,9-tetrahydropyrimido[2,1-c][1,4]oxazine-2-carbothioamide (0.04 g, 0.116 mmol, 1.0 equiv) in acetonitrile (1.2 mL) under a nitrogen atmosphere, was added MeI (0.011 mL, 0.174 mmol, 1.5 equiv). The reaction was heated at 50° C. (oil bath) for 1 h. The reaction was then cooled to ambient temperature and concentrated in vacuo. 2-(4-Fluorophenyl)acetohydrazide (0.058 g, 0.35 mmol, 3 equiv) was then added to the residue followed by methanol (1 mL) and the slurry was heated at 70° C. (oil bath). After stirring 1 h, the reaction was cooled to ambient temperature and concentrated in vacuo. DMF (1 mL) was added to the residue and the solution was heated at 150° C. (oil bath) for 3.5 h. The reaction was then cooled to ambient temperature and stirred 3 d. The reaction was heated at 140° C. (oil bath) for 2 h. The reaction was cooled to ambient temperature and concentrated in vacuo. The residue was added to a saturated aqueous solution of NaHCO$_3$ and extracted with CH$_2$Cl$_2$ (×2). The combined CH$_2$Cl$_2$ extracts were dried (Na$_2$SO$_4$) and then concentrated in vacuo. The crude product was purified by reverse phase preparatory HPLC to provide the title compound (0.021 g, 49% yield) as a gray solid. $^1$H NMR (400 MHz, CDCl$_3$) δ ppm 7.99 (s, 2H), 7.21-7.39 (m, 2H), 7.00 (t, J=8.69 Hz, 2H), 4.17 (s, 2H), 4.05 (s, 4H), 1.62 (s, 6H); LCMS (ES+, (M+H)$^+$) m/z 372.16.

Example 5

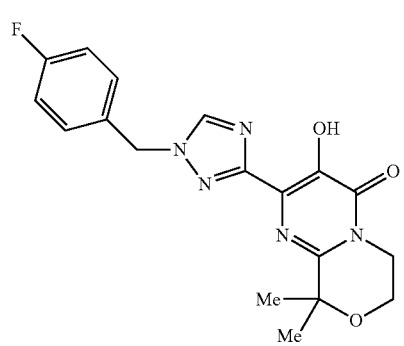 [SMILES: CC1(C)OCCn2c1nc(-c1ncn(Cc3ccc(F)cc3)n1)c(O)c2=O]

2-(1-(4-Fluorobenzyl)-1H-1,2,4-triazol-3-yl)-3-hydroxy-9,9-dimethyl-6,7-dihydropyrimido[2,1-c][1,4]oxazin-4(9H)-one. To a solution of 3-(benzyloxy)-9,9-dimethyl-4- oxo-4,6,7,9-tetrahydropyrimido[2,1-c][1,4]oxazine-2-carbothioamide (0.042 g, 0.122 mmol, 1.0 equiv) in acetonitrile (1.2 mL) under a nitrogen atmosphere, was added MeI (0.038 mL, 0.61 mmol, 5 equiv). The reaction was heated at 40° C. (oil bath) for 1 h. The reaction was then cooled to ambient temperature and concentrated in vacuo. N-(4-Fluorobenzyl)formohydrazide (0.045 g, 0.268 mmol, 2.2 equiv) was then added to the residue followed by DMF (1.5 mL) and the solution was heated at 140° C. (oil bath). After stirring 1 h, the reaction was cooled to ambient temperature stirred 17 h. The reaction was added to a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. The crude product was purified by reverse phase preparatory HPLC and trituration from ether to provide the title compound (0.024 g, 53% yield) as an off-white solid. $^1$H NMR (400 MHz, CDCl$_3$) δ ppm 8.10 (s, 1H), 7.29-7.35 (m, 2H), 7.07-7.14 (m, 2H), 5.44 (s, 2H), 4.02-4.10 (m, 4H), 1.68 (s, 6H); LCMS (ES+, (M+H)$^+$) m/z 372.20.

Example 6

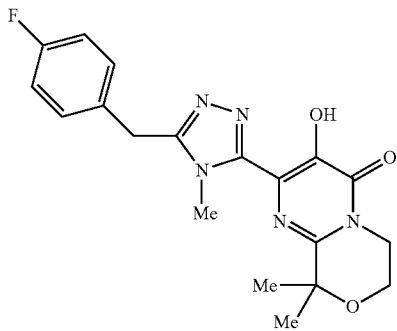 [SMILES: Cn1c(Cc2ccc(F)cc2)nnc1-c1nc2n(c(=O)c1O)CCOC2(C)C]

2-(5-(4-Fluorobenzyl)-4-methyl-4H-1,2,4-triazol-3-yl)-3-hydroxy-9,9-dimethyl-6,7-dihydropyrimido[2,1-c][1,4]oxazin-4(9H)-one. To a solution of 3-(benzyloxy)-N,9,9-trimethyl-4-oxo-4,6,7,9-tetrahydropyrimido[2,1-c][1,4]oxazine-2-carbothioamide (0.1 g, 0.278 mmol, 1.0 equiv) in acetonitrile (0.9 mL) under a nitrogen atmosphere, was added MeI (0.070 mL, 1.11 mmol, 4 equiv). The reaction was heated at 50° C. (oil bath) for 45 min. The reaction was then cooled to ambient temperature and concentrated in vacuo. 2-(4-Fluorophenyl)acetohydrazide (0.14 g, 0.84 mmol, 3 equiv) was then added to the residue followed by DMF (2 mL) and the slurry was heated at 140° C. (oil bath). After stirring 16 h, the reaction was cooled to ambient temperature and concentrated in vacuo. The residue was added to a saturated aqueous solution of NaHCO$_3$ and extracted with CH$_2$Cl$_2$ (×3). The combined CH$_2$Cl$_2$ extracts were dried (Na$_2$SO$_4$) and then concentrated in vacuo. The crude product was treated with DMF (~1.5 mL). After trying to dissolve material, the insoluble portion was filtered and washed with methanol to provide the title compound (0.024 g, 22% yield) as a white solid. $^1$H NMR (400 MHz, CDCl$_3$) δ ppm 7.21 (dd, J=8.81, 5.29 Hz, 2H), 7.03 (t, J=8.69 Hz, 2H), 4.24 (s, 2H), 4.04 (q, J=2.77 Hz, 4H), 3.93 (s, 3H), 1.57 (s, 6H); LCMS (ES+, (M+H)$^+$) m/z 386.22.

Example 7

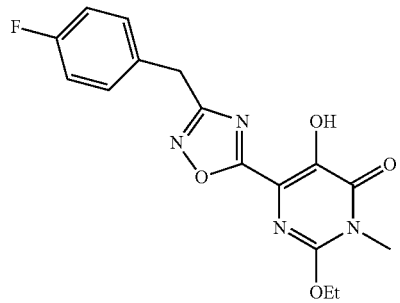 [SMILES: CCOc1nc(-c2nc(Cc3ccc(F)cc3)no2)c(O)c(=O)n1C]

2-Ethoxy-6-(3-(4-fluorobenzyl)-1,2,4-oxadiazol-5-yl)-5-hydroxy-3-methylpyrimidin-4(3H)-one. A yellow solution of 5-(benzyloxy)-2-ethoxy-6-(3-(4-fluorobenzyl)-1,2,4-oxadiazol-5-yl)-3-methylpyrimidin-4(3H)-one (0.150 g, 0.3421 mmol) in TFA (5 mL) was stirred 6 h at room temperature. Then, the reaction mixture was concentrated and the resulting yellow solid was heated with 1:1 EtOH/H$_2$O and filtered to afford the title compound (0.11 g, 97%) as pale yellow solid. $^1$HNMR (500 MHz, CDCl$_3$) δ: 9.49 (1H, s), 7.30 (2H, dd, J=8.4, 5.4 Hz), 7.02 (2H, t, J=8.6 Hz), 4.52 (2H, q, J=7.0 Hz), 4.15 (2H, s), 3.49 (3H, s), 1.44 (3H, t, J=7.0 Hz). HRMS (M+H) calcd for C$_{16}$H$_{16}$N$_4$O$_4$F: 347.1156. found: 347.3845. Anal calcd for C$_{16}$H$_{15}$N$_4$O$_4$F: C, 55.49; H, 4.36; N, 16.17; F, 5.48. found: C, 55.14; H, 4.32; N, 15.66; F, 5.85.

Example 8

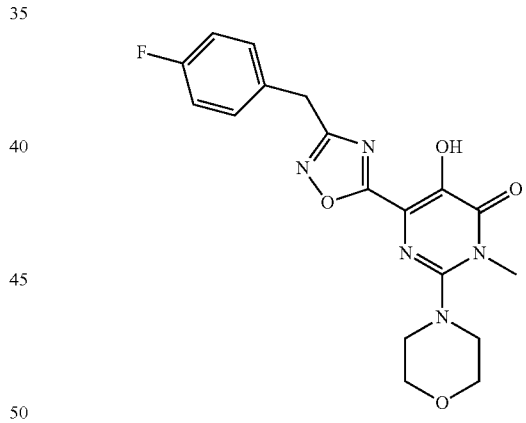

6-(3-(4-Fluorobenzyl)-1,2,4-oxadiazol-5-yl)-5-hydroxy-3-methyl-2-morpholinopyrimidin-4(3H)-one. A yellow solution of 5-(benzyloxy)-6-(3-(4-fluorobenzyl)-1,2,4-oxadiazol-5-yl)-3-methyl-2-morpholinopyrimidin-4(3H)-one (0.216 g, 0.45 mmol) in TFA (10 mL) was stirred 8 h at room temperature. The reaction mixture was then concentrated and the resulting yellow oil was dissolved in MeOH and concentrated to give pale yellow slurry which was triturated with water and filtered to afford the title compound (0.141 g, 80% yield) as a pale off-white solid. $^1$HNMR (500 MHz, CDCl$_3$) δ: 9.62 (1H, s), 7.30 (2H, dd, J=8.4, 5.4 Hz), 7.01 (2H, t, J=8.6 Hz), 4.15 (2H, s), 3.85-3.83 (4H, m), 3.58 (3H, s), 3.19-3.17 (4H, m). HRMS (M+H) calcd for C$_{18}$H$_{19}$N$_5$O$_4$F: 388.1421. found: 388.2924. Anal calcd for C$_{18}$H$_{18}$N$_5$O$_4$F: C, 55.81; H, 4.68; N, 18.08; F, 4.90. found: C, 56.16; H, 4.96; N, 17.40; F, 4.94.

Example 9

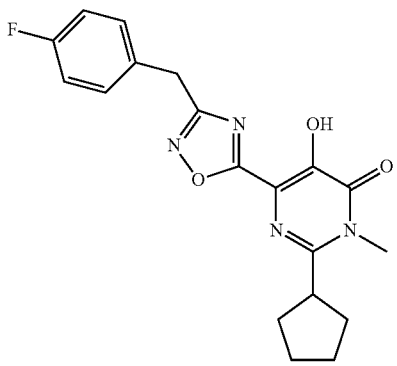 [SMILES: Cn1c(C2CCCC2)nc(-c2nc(Cc3ccc(F)cc3)no2)c(O)c1=O]

2-Cyclopentyl-6-(3-(4-fluorobenzyl)-1,2,4-oxadiazol-5-yl)-5-hydroxy-3-methylpyrimidin-4(3H)-one. A solution of 5-(benzyloxy)-2-cyclopentyl-6-(3-(4-fluorobenzyl)-1,2,4-oxadiazol-5-yl)-3-methylpyrimidin-4(3H)-one (0.248 g, 0.54 mmol) in TFA (5 mL) was stirred 4 h at room temperature. The resulting yellow reaction mixture was then concentrated and the residue was crystallized from EtOH/H$_2$O to afford the title (0.184 g, 92% yield) as a yellow solid. $^1$HNMR (500 MHz, CDCl$_3$) δ: 9.74 (1H, s), 7.30 (2H, dd, J=8.2, 5.5 Hz), 7.01 (2H, t, J=8.6 Hz), 4.15 (2H, s), 3.64 (3H, s), 3.21-3.15 (1H, m), 2.04-2.00 (4H, m), 1.89-1.82 (2H, m), 1.72-1.64 (2H, m). HRMS (M+H) calcd for C$_{19}$H$_{20}$N$_4$O$_3$F: 371.1520. found: 371.1535. Anal calcd for C$_{19}$H$_{19}$N$_4$O$_3$F: C, 61.61; H, 5.17; N, 15.12; F, 5.13. found: C, 61.92; H, 5.54; N, 14.87; F, 5.10.

Example 10

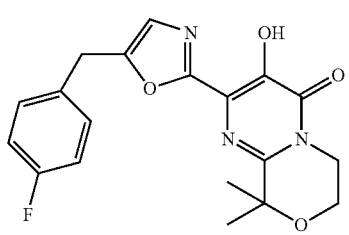 [SMILES: CC1COC(C)(C)c2nc(-c3ncc(Cc4ccc(F)cc4)o3)c(O)c(=O)n21]

2-(5-(4-Fluorobenzyl)oxazol-2-yl)-3-hydroxy-9,9-dimethyl-6,7-dihydropyrimido[2,1-c][1,4]oxazin-4(9H)-one. A mixture of 3-(benzyloxy)-N-(3-(4-fluorophenyl)-2-oxopropyl)-9,9-dimethyl-4-oxo-4,6,7,9-tetrahydropyrimido[2,1-c][1,4]oxazine-2-carboxamide (0.16 g, 0.3337 mmol) and POCl$_3$ (2 mL) in toluene (15 mL) was heated at reflux for 5 h, then cooled, concentrated and the resulting residue taken up in EtOAc (50 mL), washed with water (2×10 mL), brine (10 mL), dried (Na$_2$SO$_4$), filtered and concentrated to give a yellow residue. Purification by preparative HPLC on C18 column using water/MeOH containing 0.1% TFA provided the title as a white solid which was crystallized from MeOH/H$_2$O to afford colorless needles. $^1$HNMR (500 MHz, CDCl$_3$) δ: 11.04-10.92 (1H, br s), 7.26 (2H, dd, J=8.6, 5.5 Hz), 7.04 (2H, t, J=8.6 Hz), 6.86 (1H, s), 4.10 (2H, s), 4.07-4.02 (4H, m), 1.65 (6H, s). HRMS (M+H) calcd for C$_{19}$H$_{19}$N$_3$O$_4$F: 372.1360. found: 372.1356. Anal calcd for C$_{19}$H$_{18}$N$_3$O$_4$F: C, 61.45; H, 4.88; N, 11.31. found: C, 61.19; H, 4.74; N, 11.14.

Example 11

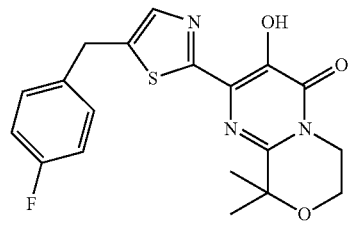 [SMILES: CC1COC(C)(C)c2nc(-c3ncc(Cc4ccc(F)cc4)s3)c(O)c(=O)n21]

2-(5-(4-Fluorobenzyl)thiazol-2-yl)-3-hydroxy-9,9-dimethyl-6,7-dihydropyrimido[2,1-c][1,4]oxazin-4(9H)-one. A solution of 3-(benzyloxy)-2-(5-(4-fluorobenzyl)thiazol-2-yl)-9,9-dimethyl-6,7-dihydropyrimido[2,1-c][1,4]oxazin-4(9H)-one (0.051 g, 0.11 mmol) in TFA (5 mL) was stirred 24 h at 40 C. Then, the reaction mixture was cooled, concentrated and purified by preparative HPLC on C18 column using water/MeOH containing 0.1% TFA as eluent to afford the title compound (0.033 g, 80% yield) as pale yellow solid. $^1$HNMR (500 MHz, CDCl$_3$) δ: 11.51 (1H, s), 7.61 (1H, s), 7.22 (2H, dd, J=8.6, 5.5 Hz), 7.03 (2H, t, J=8.6 Hz), 4.17 (2H, s), 4.06-4.01 (4H, m), 1.60 (6H, s). HRMS (M+H) calcd for C$_{19}$H$_{19}$N$_3$O$_3$FS: 388.1131. found: 388.1118. Anal calcd for C$_{19}$H$_{18}$N$_3$O$_3$FS: C, 58.90; H, 4.68; N, 10.84. found: C, 58.87; H, 4.47; N, 10.87.

Example 12

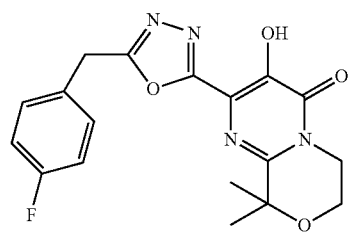 [SMILES: CC1COC(C)(C)c2nc(-c3nnc(Cc4ccc(F)cc4)o3)c(O)c(=O)n21]

2-(5-(4-Fluorobenzyl)-1,3,4-oxadiazol-2-yl)-3-hydroxy-9,9-dimethyl-6,7-dihydropyrimido[2,1-c][1,4]oxazin-4(9H)-one. A solution of 3-(benzyloxy)-2-(5-(4-fluorobenzyl)-1,3,4-oxadiazol-2-yl)-9,9-dimethyl-6,7-dihydropyrimido[2,1-c][1,4]oxazin-4(9H)-one (0.071 g, 0.15 mmol) in TFA (5 mL) was stirred 22 h at room temperature. The reaction mixture was then concentrated and purified by preparative HPLC on a C18 column using water/MeOH containing 0.1% TFA as eluent to afford the title compound (0.035 g, 60% yield) as white solid. $^1$HNMR (500 MHz, CDCl$_3$) δ: 9.71 (1H, s), 7.35 (2H, dd, J=8.6, 5.5 Hz), 7.06 (2H, t, J=8.6 Hz), 4.30 (2H, s), 4.07-4.03 (4H, m), 1.63 (6H, s). HRMS (M+H) calcd for C$_{18}$H$_{18}$N$_4$O$_4$F: 373.1312. found: 373.1326. Anal calcd for C$_{18}$H$_{17}$N$_4$O$_4$F: C, 58.06; H, 4.60; N, 15.04. found: C, 57.88; H, 4.72; N, 14.87.

We claim:
1. A compound of Formula I

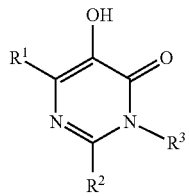

wherein:
- $R^1$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl; $R^1$ is substituted with 1 benzyl moiety which is further substituted with 0-3 substituents selected from halo and alkyl; and $R^1$ is substituted with 0-2 alkyl substituents;
- $R^2$ is alkoxy, cycloalkyl, or morpholinyl;
- $R^3$ is alkyl;
- or $R^2$ and $R^3$ taken together is

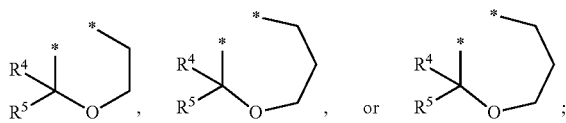

- $R^4$ is hydrogen or alkyl; and
- $R^5$ is hydrogen or alkyl;
- or $R^4$ and $R^5$ taken together is $C_{3-6}$alkylene or $CH_2CH_2OCH_2CH_2$;
- or a pharmaceutically acceptable salt thereof.

2. A compound of claim 1 where
- $R^1$ is triazolyl, oxadiazolyl, imidazolyl, oxazolyl, or thiazolyl; $R^1$ is substituted with 1 benzyl moiety substituted with 1 halo substituent; and $R^1$ is substituted with 0-1 alkyl substituents;
- $R^2$ is alkoxy, cycloalkyl, or morpholinyl;
- $R^3$ is alkyl;
- or $R^2$ and $R^3$ taken together is

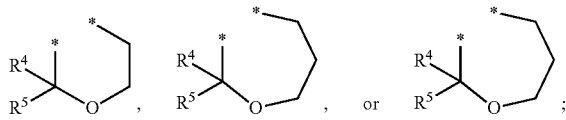

- $R^4$ is alkyl; and
- $R^5$ is alkyl;
- or a pharmaceutically acceptable salt thereof.

3. A compound of claim 2 where
- $R^1$ is triazolyl, N-methyltrizolyl, oxadiazolyl, imidazolyl, N-methylimidazolyl, oxazolyl, or thiazolyl, and is substituted with 1 p-fluorobenzyl moiety;
- $R^2$ is ethoxy, cyclopentyl, or morpholinyl;
- $R^3$ is methyl;

or $R^2$ and $R^3$ taken together is

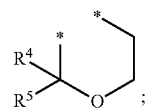

- $R^4$ is methyl; and
- $R^5$ is methyl;
- or a pharmaceutically acceptable salt thereof.

4. A compound of claim 1 where $R^1$ is triazolyl, oxadiazolyl, imidazolyl, oxazolyl, or thiazolyl; $R^1$ is substituted with 1 benzyl moiety which is substituted with 0-3 substituents selected from halo and alkyl; and $R^1$ is substituted with 0-2 alkyl substituents.

5. A compound of claim 1 where $R^2$ and $R^3$ taken together is

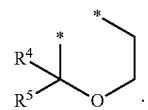

6. A compound of claim 1 where $R^4$ and $R^5$ are methyl.
7. A compound of claim 1 where $R^4$ and $R^5$ taken together is propylene, butylene, or $CH_2CH_2OCH_2CH_2$.
8. A compound of claim 1 selected from the group consisting of
- 2-(5-(4-Fluorobenzyl)-1H-imidazol-2-yl)-3-hydroxy-9,9-dimethyl-6,7-dihydropyrimido[2,1-c][1,4]oxazin-4(9H)-one;
- 2-(5-(4-Fluorobenzyl)-1-methyl-1H-imidazol-2-yl)-3-hydroxy-9,9-dimethyl-6,7-dihydropyrimido[2,1-c][1,4]oxazin-4(9H)-one;
- 2-(1-(4-Fluorobenzyl)-1H-imidazol-4-yl)-3-hydroxy-9,9-dimethyl-6,7-dihydropyrimido[2,1-c][1,4]oxazin-4(9H)-one;
- 2-(5-(4-Fluorobenzyl)-4H-1,2,4-triazol-3-yl)-3-hydroxy-9,9-dimethyl-6,7-dihydropyrimido[2,1-c][1,4]oxazin-4(9H)-one;
- 2-(1-(4-Fluorobenzyl)-1H-1,2,4-triazol-3-yl)-3-hydroxy-9,9-dimethyl-6,7-dihydropyrimido[2,1-c][1,4]oxazin-4(9H)-one;
- 2-(5-(4-Fluorobenzyl)-4-methyl-4H-1,2,4-triazol-3-yl)-3-hydroxy-9,9-dimethyl-6,7-dihydropyrimido[2,1-c][1,4]oxazin-4(9H)-one;
- 2-(5-(4-Fluorobenzyl)oxazol-2-yl)-3-hydroxy-9,9-dimethyl-6,7-dihydropyrimido[2,1-c][1,4]oxazin-4(9H)-one;
- 2-(5-(4-Fluorobenzyl)thiazol-2-yl)-3-hydroxy-9,9-dimethyl-6,7-dihydropyrimido[2,1-c][1,4]oxazin-4(9H)-one; and
- 2-(5-(4-Fluorobenzyl)-1,3,4-oxadiazol-2-yl)-3-hydroxy-9,9-dimethyl-6,7-dihydropyrimido[2,1-c][1,4]oxazin-4(9H)-one;
- or a pharmaceutically acceptable salt thereof.

9. A compound of claim 1 selected from the group consisting of
- 2-Ethoxy-6-(3-(4-fluorobenzyl)-1,2,4-oxadiazol-5-yl)-5-hydroxy-3-methylpyrimidin-4(3H)-one;
- 6-(3-(4-Fluorobenzyl)-1,2,4-oxadiazol-5-yl)-5-hydroxy-3-methyl-2-morpholinopyrimidin-4(3H)-one; and
- 2-Cyclopentyl-6-(3-(4-fluorobenzyl)-1,2,4-oxadiazol-5-yl)-5-hydroxy-3-methylpyrimidin-4(3H)-one;
- or a pharmaceutically acceptable salt thereof.

10. A composition useful for treating HIV infection comprising a therapeutic amount of a compound of claim 1 and a pharmaceutically acceptable carrier.

11. The composition of claim 10 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

12. A method for treating HIV infection comprising administering a therapeutically effective amount of a compound of claim 1, or a pharmaceutically acceptable salt thereof, to a patient in need thereof.

13. The method of claim 12 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *

UNITED STATES PATENT AND TRADEMARK OFFICE
CERTIFICATE OF CORRECTION

PATENT NO. : 8,383,639 B2  Page 1 of 1
APPLICATION NO. : 12/901147
DATED : February 26, 2013
INVENTOR(S) : B. Narasimhulu Naidu et al.

It is certified that error appears in the above-identified patent and that said Letters Patent is hereby corrected as shown below:

In the Claims:

Claim 3:

Column 41, line 62, change "N-methyltrizolyl," and insert -- N-methyltriazolyl, --.

Signed and Sealed this
Sixth Day of May, 2014

Michelle K. Lee
*Deputy Director of the United States Patent and Trademark Office*